United States Patent
Du et al.

(10) Patent No.: US 12,241,107 B2
(45) Date of Patent: Mar. 4, 2025

(54) METHOD OF CONTROLLING THE PINK COLOR GENERATED DURING ANTIBODY MANUFACTURING

(71) Applicant: BRISTOL-MYERS SQUIBB COMPANY, Princeton, NJ (US)

(72) Inventors: Cheng Du, West Roxbury, MA (US); Ameya Umesh Borwankar, San Francisco, CA (US); Joon Chong Yee, Acton, MA (US); Zhijun Tan, Acton, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 1153 days.

(21) Appl. No.: 16/612,175

(22) PCT Filed: May 8, 2018

(86) PCT No.: PCT/US2018/031542
§ 371 (c)(1),
(2) Date: Nov. 8, 2019

(87) PCT Pub. No.: WO2018/208743
PCT Pub. Date: Nov. 15, 2018

(65) Prior Publication Data
US 2023/0103511 A1    Apr. 6, 2023

Related U.S. Application Data

(60) Provisional application No. 62/503,615, filed on May 9, 2017.

(51) Int. Cl.
*C12P 21/00*    (2006.01)
*C07K 16/00*    (2006.01)

(52) U.S. Cl.
CPC .............. *C12P 21/00* (2013.01); *C07K 16/00* (2013.01); *C07K 2317/14* (2013.01)

(58) Field of Classification Search
None
See application file for complete search history.

(56) References Cited

U.S. PATENT DOCUMENTS

| | | | | |
|---|---|---|---|---|
| 2005/0000908 A1* | 1/2005 | Karlsson | ............. | C02F 1/722 210/759 |
| 2007/0282293 A1* | 12/2007 | Janus | ............. | A01N 1/0263 604/404 |
| 2012/0183531 A1 | 7/2012 | Lucas et al. | | |

FOREIGN PATENT DOCUMENTS

| | | | | |
|---|---|---|---|---|
| WO | WO-2006060083 A1 * | 6/2006 | ....... | A61K 39/39525 |
| WO | WO2009009523 A2 | 1/2009 | | |
| WO | WO2015085003 A1 | 6/2015 | | |

OTHER PUBLICATIONS

Sreedhara et al. European J. of Pharmaceutics and Biophamaceutics, vol. 10, p. 38-46, 2016.*
Derfus G.E. et al.: "Red colored IgG4 caused by vitamin B12 from cell culture media combined with disulfide reduction at harvest.", MABS, vol. 6, No. 3, Feb. 19, 2014 (Feb. 19, 2014), pp. 679-688, XP002784132.
Du, C. et al.: "Using hydrogen peroxide to prevent antibody disulfine bond reduction during manufacturing process", MABS, vol. 10, No. 3, Jan. 23, 2018 (Jan. 23, 2018), pp. 500-510, XP002784131.
Du, C. et al.: "Vitamin B12 association with mAbs: Mechanism and potential mitigation strategies.", Biotech. Bioeng., vol. 115, Dec. 19, 2017 (Dec. 19, 2017), pp. 900-909, XP002784130.
International Search Report for PCTUS2018031542 mailed on Nov. 9, 2018, 8 pages.
Juzeniene Asta et al: "Photodegradation of cobalamins in aqueous solutions and in human blood", Journal of Photochemistry and Photobiology B: Biology, vol. 122, Mar. 14, 2013 (Mar. 14, 2013), pp. 7-14, XP028593486.
Luo D., Smith S.W. & Anderson B.D.: "Kinetics and mechanism of the reaction of cysteine and hydrogen peroxide in aqueous solution.", J. Pharm. Sci., vol. 94, No. 2, 2005, pp. 304-316, XP002784133.
Prentice K.M. et al.: "Hydroxocobalamin association during cell culture results in pink therapeutic proteins.", MABS, vol. 5, No. 6, Jul. 26, 2013 (Jul. 26, 2013), pp. 974-981, XP002784134.
Hanglogten, "You Don't Need Reproducible Research Until You Do", PHCbi Cell Culture Incubators: CO2 and Multigas Incubators for Precise Cell Culture Reproducibility, Biotechnology and Engineering, 114(7):1469-1477, 2017.
Kao, et al., "You Don't Need Reproducible Research Until You Do", Minimize uncertainty with PHCbi brand products, Biotechnology and Bioengineering: Mechanism of Antibody Reduction in Cell Culture Production Processes, 2010, vol. 107 (4):622-632.
Koterba, et al., "Thioredoxin 1 is responsible for antibody disulfide reduction in CHO cell culture", Journal of Biotechnology, 2012, vol. 157:261-267.
Trexler-Schmidt, "You Don't Need Reproducible Research Until You Do", PHCbi Cell Culture Incubators: CO2 and Multigas Incubators for Precise Cell Culture Reproducibility: Cell-IQ TM and CytoGrow Incubators, Biotechnology and Bioengineering, 106(3):452-461, 2010.
Nowak, Christine et al., "Forced degradation of recombinant monoclonal antibodies: A practical guide", MABS, 2017, vol. 9, No. 8, pp. 1217-1230.
Sidorova, M.V., et al., "The Use of Hydrogen Peroxide for Closing Disulfide Bridges in Peptides", Russian Journal of Bioorganic Chemistry, vol. 30, No. 2, 2004, pp. 101-110.

(Continued)

*Primary Examiner* — Yunsoo Kim
(74) *Attorney, Agent, or Firm* — Xiangyu Liu

(57) ABSTRACT

The invention is a method of preventing the generation of pink color during antibody manufacturing by either preventing the reduction of antibodies during manufacturing and harvest or inhibiting the conversion of cyanocobalamin (CN-Cbl) to hydroxocobalamin (HO-Cbl) during manufacturing and harvest. Replacement of white light in the cell culture media preparation and storage areas with red light inhibits the conversion of CN-Cbl to HO-Cbl. Addition of peroxides to the clarified bulk at harvest inhibits reduction of the antibody disulfide bonds.

3 Claims, 22 Drawing Sheets
Specification includes a Sequence Listing.

(56) References Cited

OTHER PUBLICATIONS

Nowak, Christine, et al., "Forced Degradation of Recombinant Monoclonal Antibodies: A Practical Guide", mTBS, 2017, vol. 9, No. 8, pp. 1217-1230.

* cited by examiner

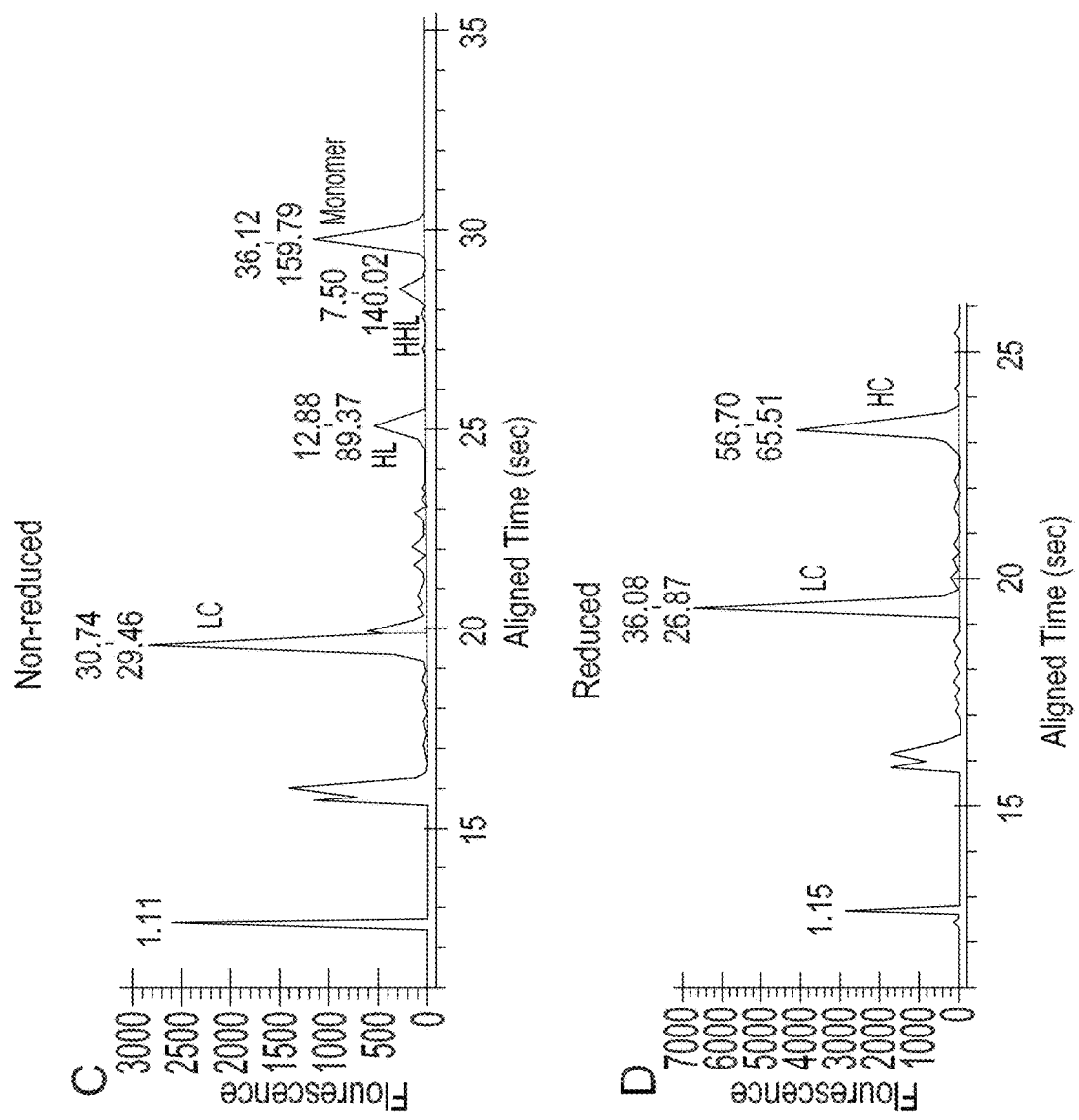

METHOD OF CONTROLLING THE PINK COLOR GENERATED DURING ANTIBODY MANUFACTURING

CROSS-REFERENCE TO RELATED APPLICATIONS

This application is a 35 U.S.C. § 371 national stage application of International Application No. PCT/US2018/031542, filed May 8, 2018, which claims the benefit of U.S. Provisional Patent Application No. 62/503,615, filed May 9, 2017, the contents of which are hereby incorporated herein in their entirety by reference.

BACKGROUND

Monoclonal antibody (mAb) therapeutics become more popular in treatment of multiple human diseases. As macromolecules, mAb bear certain heterogeneity due to a wide range of post-translational modifications. Successful control of manufacturing process is critical for ensuring product quality and safety and lot to lot consistency of therapeutic proteins. In fact, the ICH Q6B guideline requires a product appearance specification.

Normal antibody manufacturing commonly has some color variation which is acceptable (Derfus G E, et. al., MAbs 2014, 6 (3):679-688, Prentice K M, et. al., MAbs 2013, 5 (6):974-981, Vijayasankaran N, et. al., Biotechnol Prog 2013, 29 (5):1270-1277, Xu J, et. al., Process Biochemistry 2014, 49:130-1394). However, color variation due to in-process impurities is a concern of lack of process control. One of the main sources of pink/red color in final drug substance has been identified as vitamin $B_{12}$-mAb complex (Derfus, 2014, Prentice, 2013). Although the nature of the interaction has not been elucidated, the attachment of vitamin $B_{12}$ to protein appears strong enough to co-elute through multiple downstream purification steps, including protein A affinity chromatograph, low-pH viral inactivation, various polishing chromatographs and ultrafiltration and diafiltration.

Antibodies are commonly produced in mammalian cells, such as Chinese hamster ovary (CHO) cells, and are secreted extracellularly into the cell culture media. At the end of the culture process, cells are separated from the culture media during the primary recovery step using methods such as centrifugation, depth filtration, or flocculation to clarify the harvest fluid. During this process, the cells often suffer various stresses, including mechanical shear, exposure to a low dissolved oxygen (DO) environment, or temperature and pH shifts. These stresses cause cell damage resulting in the release of undesired intracellular components into the clarified fluid. These cytosolic components, such as lipids and enzymes, can potentially affect product quality, and must be carefully monitored or removed. For example, the release of intracellular reducing agents can lead to the reduction of antibody disulfide bonds (Mun M., et. al. Biotechnol Bioeng 2015; 112:734-742; Ruaudel J, et. al. BMC Proceedings 2015; 9 (Suppl 9):P24; Mullan B, et. al. BMC Proc. 2011; 5 (Suppl 8):P110; Trexler-Schmidt M, et. al. Biotechnol Bioeng. 2010; 106:452-461; Koterba, K L, et. al. J Biotechnol. 2012; 157:261-267; Handlogten M W, et. al. Biotechnol Bioeng. 2017; 114:1469-1477; Hutchinson N, et. al. Biotechnol Bioeng. 2006; 95:483-491).

During the manufacturing process, extensive reduction of antibodies has been observed after harvest operation and/or Protein A chromatography. Multiple process parameters may have an impact on the extent of antibody reduction. For example, maintaining high levels of dissolved oxygen (DO) during harvest is vital to keep antibody molecules intact (Mun M. 2015; Trexler-Schmidt M, 2010). Mechanical shear forces, which cause cell lysis and cellular components to leak into harvest fluids, also significantly contributes to the reduction (Kao Y H, et. al. Biotechnol Bioeng. 2010; 107:622-632; Hutterer K M, et. al. MAbs. 2013; 5:608-613). Other process parameters, such as harvest hold time (Chung W K, et. al. Biotechnol Bioeng. 2017; 114:1264-12741), media components (such as copper ions, cysteine/cysteine) and pH and temperature, (Trexler-Schmidt M, 2010; Chung, 2017) also have an effect on the extent of disulfide reduction.

In order to ensure antibody product quality, manufacturing in-process controls are necessary to control low molecular weight (LMW) species formed from reduction of antibody disulfide bonds. As a result, several strategies have been proposed in recent years to control disulfide reduction. Chemical inhibitors have been tested to prevent antibody reduction, including pre- and post-harvest treatment with anti-reduction agents, such as cupric sulfate (Chaderjian W B, et. al. Biotechnol Prog. 2005; 21:550-553), ethylenediaminetetraacetic acid (EDTA), thioredoxin inhibitors, (U.S. Pat. No. 8,574,869) cysteine, methyl blue (WO 2015/085003) and coenzyme Q analogs (Li W W, et. al. J Am Chem Soc. 2005; 127:6140-614). Although knowledge and methods surrounding mitigation strategies has increased over years, implementation of these methods in production is not without difficulties, such as introduction of chemical byproducts that need to be removed by chromatography steps, increased processing time, and the risk of off-target modifications or damage to the antibody product.

SUMMARY OF THE INVENTION

The invention is a method of preventing the generation of pink color during antibody manufacturing by either 1) preventing the reduction of antibodies during manufacturing and harvest or 2) inhibiting the conversion of cyanocobalamin (CN-Cbl) to hydroxocobalamin (HO-Cbl) during manufacturing and harvest, or 3) both, preventing the reduction of antibodies and inhibiting conversion of cyanocobalamin to hydroxocobalamin during manufacturing and harvest.

In one embodiment of the invention, the CN-Cbl conversion to HO-Cbl is inhibited by preventing media exposure to visible light during one or more times selected from media preparation, media storage, antibody production, and antibody harvest.

In one embodiment of the invention, CN-Cbl is exposed to only UVA light during one or more times selected from media preparation, media storage, antibody production, and antibody harvest.

In one embodiment of the invention, CN-Cbl is exposed to only red light (>600 nm) during media preparation, media storage, and optionally during antibody production, and antibody harvest.

In one embodiment of the invention, reduction of the antibody disulfide bonds is prevented by adding hydrogen peroxide to the clarified bulk at harvest.

Another embodiment of the invention is a method of inhibiting vitamin $B_{12}$ from binding to antibodies during manufacture comprising 1) preventing reduction of antibody disulfide bonds during manufacturing and harvest, or 2) inhibiting conversion of CN-Cbl to HO-Cbl during cell culture media preparation, media storage, cell culture process or antibody harvest.

Another embodiment of the invention is a method for the production of antibodies comprising 1) preparing and storing the cell culture media under red light (>600 nm) conditions, 2) culturing cells which produce the antibody of interest under red light conditions, 3) harvesting the antibody from the cell culture under red light conditions, and 4) adding hydrogen peroxide to the harvest solution.

Another embodiment of the invention is a method for production of antibodies comprising 1) preparing and storing the cell culture media under red light (>600 nm) conditions, 2) culturing cells which produce the antibody of interest under red light conditions, and 3) harvesting the antibody of interest from the cell culture under red light conditions.

Another embodiment of the invention is a method for production of antibodies comprising 1) culturing cells which produce the antibody of interest, 2) harvesting the antibody of interest from the cell culture, and 3) adding hydrogen peroxide to the harvest solution.

DETAILED DESCRIPTION

Process control of biologics manufacturing is critical for ensuring product quality and safety and lot to lot consistency of therapeutic proteins. Understanding of the mechanism of color generation during manufacturing is critical to develop control strategy. The inventors discovered that the generation of pink color during antibody manufacturing is a second-order reaction dependent on concentrations of both free sulfhydryl groups on reduced antibodies and hydroxocobalamin, the active form of vitamin $B_{12}$. Both reactants are necessary and neither one alone is sufficient to generate pink color. The invention is a method of preventing the generation of pink color during antibody manufacturing by either 1) preventing the reduction of antibodies during manufacturing and harvest or 2) inhibiting the conversion of cyanocobalamin (CN-Cbl) to hydroxocobalamin (HO-Cbl) during manufacturing and harvest. Alternatively, the invention is a method of preventing the generation of pink color during antibody manufacturing by 1) preventing the reduction of antibodies during manufacturing and harvest and 2) inhibiting the conversion of cyanocobalamin to hydroxocobalamin during manufacturing and harvest.

Figure 3:
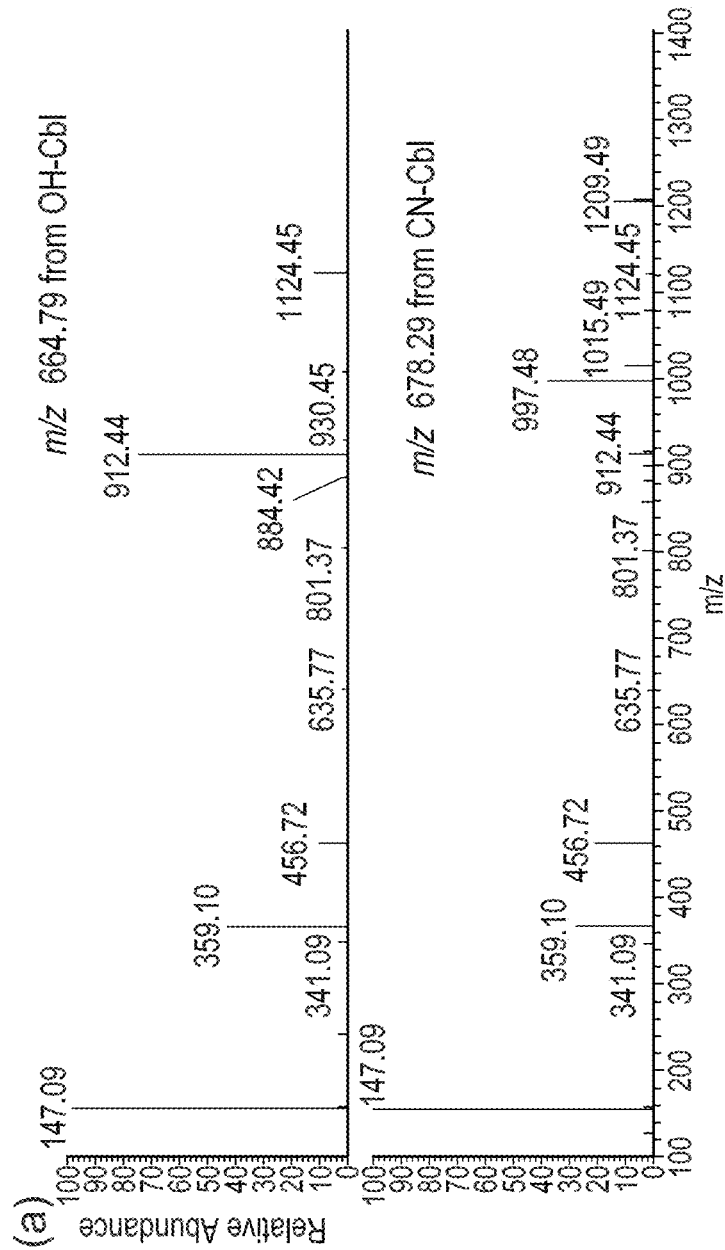
FIG. 3A-3C show the mass spectral data for identification of vitamin B12 conjugation. (3A) MS/MS spectra of m/z=664.79 from HO-Cbl and m/z=678.29 from CN-Cbl. (3B) MS/MS spectra of peptide-cobalamin complexes L19-Cobalamin and L18-19-Cobalamin. (3C) illustration of IgG4 antibody disulfide bonds. The cysteine residues that bind to vitamin B12 are numbered and pairs of cysteine residues forming disulfide bonds are circled.
Figure 3:
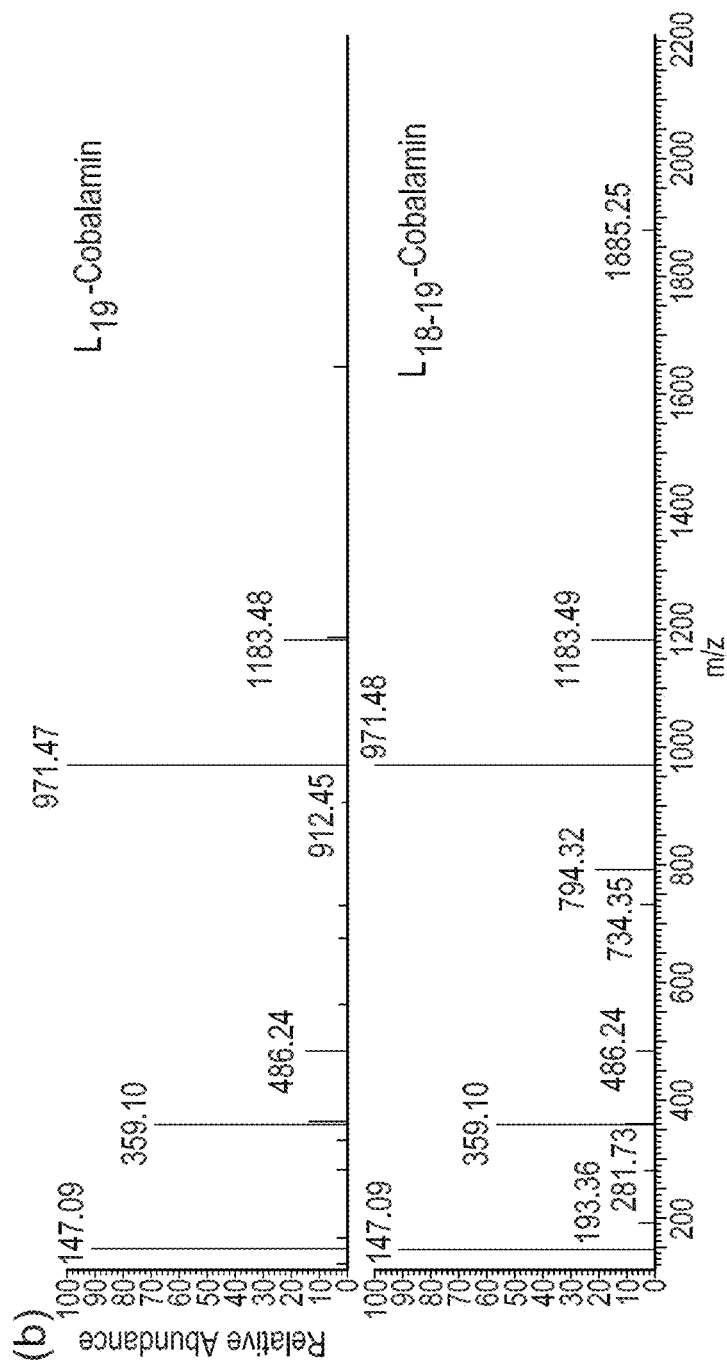
Figure 3:
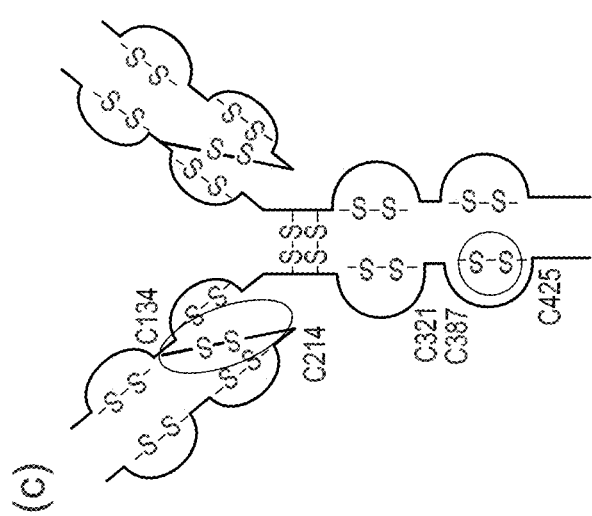

The inventors discovered that the active form of vitamin $B_{12}$ attaches to the free sulfhydryl group of the cysteine located at heavy chain 134 (HC134), light chain 214 (LC214), heavy chain 321 (HC321), heavy chain 367 (HC367), and heavy chain 425 (HC425). The five cysteine residues are distributed among both the Fab and the Fc regions. There are two pairs of disulfide bonds among these five cysteine residues, LC214 with HC134 and HC367 with HC425 (FIG. 3c). When these particular disulfide bonds are reduced during the manufacturing and harvest, both cysteine residues in the disulfide pair have equal accessibility for hydroxocobalamin attachment.

As used herein, "cyanocobalamin" and "CN-Cbl" are used interchangeably and refer to the vitamin $B_{12}$ (VB12) component of the cell culture media. Likewise, "hydroxocobalamin" and "HO-Cbl" are used interchangeably and refer to the active form of vitamin $B_{12}$ (VB12) in the cell culture media available to bind the reduced antibodies during manufacturing and harvest.

Antibodies are commonly produced in mammalian cells, such as Chinese hamster ovary (CHO) cells, and are secreted extracellularly into the cell culture media. At the end of the cell culture process, cells are separated from the culture media during the primary recovery step using methods such as centrifugation, depth filtration, or flocculation to clarify the harvest fluid.

As used herein, "clarified bulk" and "CB" are used interchangeably and refer to the solution collected after the primary recovery step, such as centrifugation, depth filtration, or flocculation, which is used to clarify the cell culture fluid.

As used herein, "cell culture media preparation" "cell culture media storage", "cell culture process" "antibody manufacture", "antibody production", and "antibody harvest", "harvest", refer to the many steps required to produce antibodies. Each step may occur in different locations within a manufacturing facility.

Use of Red Color Light in Manufacturing Environment as a Control Strategy of Pink Color.

Since both hydroxocobalamin and reduced antibodies are required for the generation of pink color products, control of either one or both factors will prevent pink color generation.

Light-induced vitamin $B_{12}$ conversion can occur during media preparation, media storage and cell culture processing. The use of transparent disposable bioprocessing bags in media preparation, storage duration, and the cell culture duration in glass bioreactors increase the risk of vitamin $B_{12}$ light exposure and conversion. General control strategies, such as using appropriate containers (for example stainless steel containers), covering with additional layer material, avoiding unnecessary light exposure, can provide protection from light. However, implementation of these strategies are not without challenges and often include additional costs.

Example 1 shows that red light does not induce CN-Cbl conversion to HO-Cbl. Reduced mAb A was spiked into culture media that had been exposed to white light, or red light or green light, or kept in the dark. After overnight incubation, the mAb was purified by Protein A column and bound vitamin $B_{12}$ was measured by ELISA assay. As shown in Table 7, the order of vitamin $B_{12}$ conjugation rates were white light>green light>red light and in dark control.

In one embodiment of the invention, cyanocobalamin conversion to hydroxocobalamin is inhibited, reduced or prevented by replacing the white light with red colored light (wavelengths>600 nm) in the areas where the cell culture media is prepared and stored, and optionally in the cell culture manufacturing and harvesting areas.

In another embodiment of the invention, cyanocobalamin conversion to hydroxocobalamin is inhibited, reduced or prevented by replacing the white light bulbs with red colored LED light bulbs (wavelengths>600 nm) in the areas where the cell culture media is prepared and stored, and optionally in the cell culture manufacturing and harvesting areas.

In another embodiment of the invention, cyanocobalamin conversion to hydroxocobalamin is inhibited, reduced or prevented by placing red color plastic sheets or alternately red color tubing over the white light bulbs in the areas where the cell culture media is prepared and stored, and optionally in the cell culture manufacturing and harvesting areas.

In another embodiment of the invention, the white light in the areas where the cell culture media is prepared and stored, and also in the cell culture manufacturing and harvesting areas is replaced with red colored light by replacing the white light bulbs with red colored LED light bulbs (wavelengths>600 nm), or placing red color plastic sheets or alternatively red color tubing over the white light bulbs.

In another embodiment of the invention, the white light in the areas where the cell culture media is prepared and stored, and also in the cell culture harvesting area is replaced with red colored light by replacing the white light bulbs with red colored LED light bulbs (wavelengths>600 nm), or placing red color plastic sheets or alternatively red color tubing over the white light bulbs.

In another embodiment of the invention, the white light in the areas where the cell culture media is prepared and stored, and also in the cell culture manufacturing area is replaced with red colored light by replacing the white light bulbs with red colored LED light bulbs (wavelengths>600 nm), or placing red color plastic sheets or alternatively red color tubing over the white light bulbs.

Preventing Antibody Reduction during Protein Harvest and Primary Recovery as a Control Strategy of Pink Color.

Since both reduced antibodies and hydroxocobalamin are required for the generation of pink color products, control of either one or both factors will prevent pink color generation.

The reduction of disulfide bonds during mAb manufacturing is an enzymatic redox reaction and the root cause of low molecular weight species (LMW) formation during the antibody manufacturing process, While the causes of LMW generation are not well understood, it is believed that the appearance of LMW results from a combinatorial effect of cell culture conditions, such as temperature, dissolved oxygen (DO), pH, viability, cell density, lysis percentage, etc., that creates a reducing environment for the antibody. This is further exacerbated by the clarified bulk (CB) holding conditions (e.g., temperature, duration, aeration), which retain the antibody in the reducing environment. The detection of LMW is usually visualized in clarified bulk or the Protein A eluate pool steps.

Figure 8:
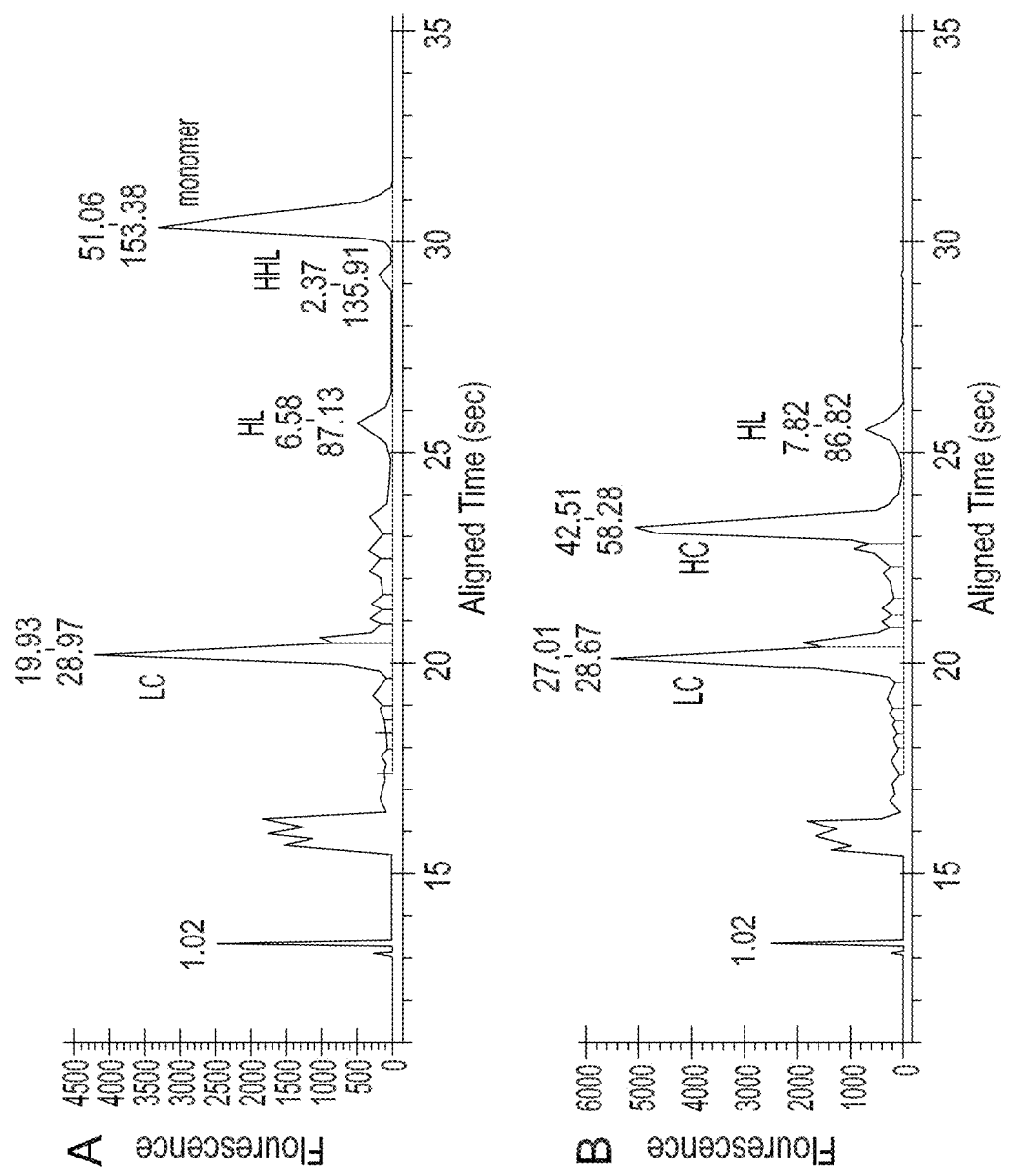
FIG. 8A-8F shows the evaluation of using hydrogen peroxide to prevent disulfide bond reduction in worst case. The tested mAb 2 CB had 100% cell lysis as described in Example 2. The holding conditions with or without air were the same as in FIG. 7. (8A) CB sample without hydrogen peroxide treatment and held with air serves as a control. (8B) CB sample without hydrogen peroxide treatment and held in airless conditions. (8C) 5 mM hydrogen peroxide was added to CB sample before holding in airless condition. (8C) 10 mM hydrogen peroxide was added to CB sample before holding in airless condition. The resulting CB samples (8A to 8D) were analyzed directly by nonreduced Caliper without Protein A purification. (8E) Summary of non-reduced Caliper results of mAb fragmentation from unpurified CB. (8F) Summary intact antibody purities from samples 8A to 8 D using purified by Protein A chromatography and analyzed by non-reduced Caliper.
Figure 8:
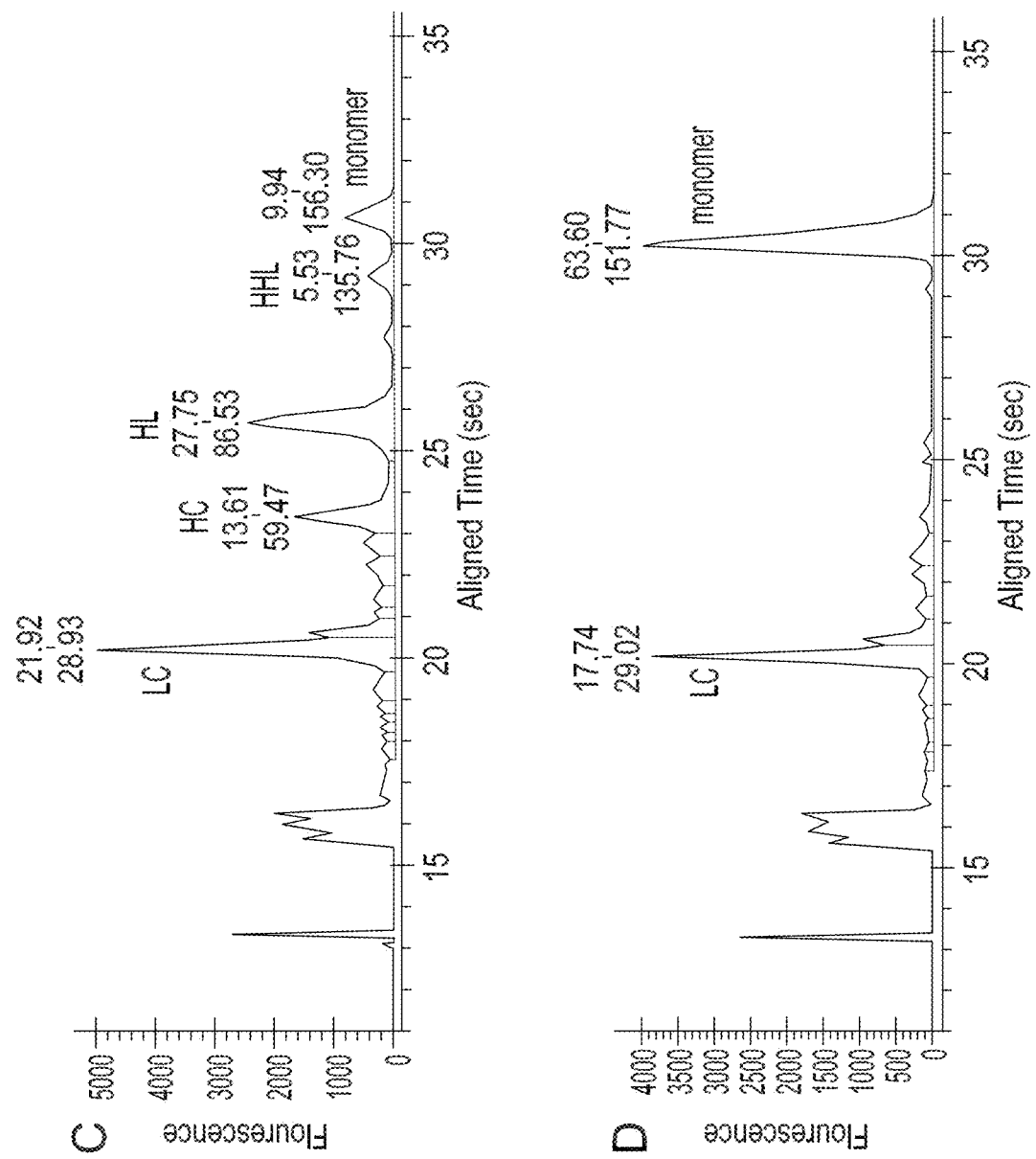
Figure 8:
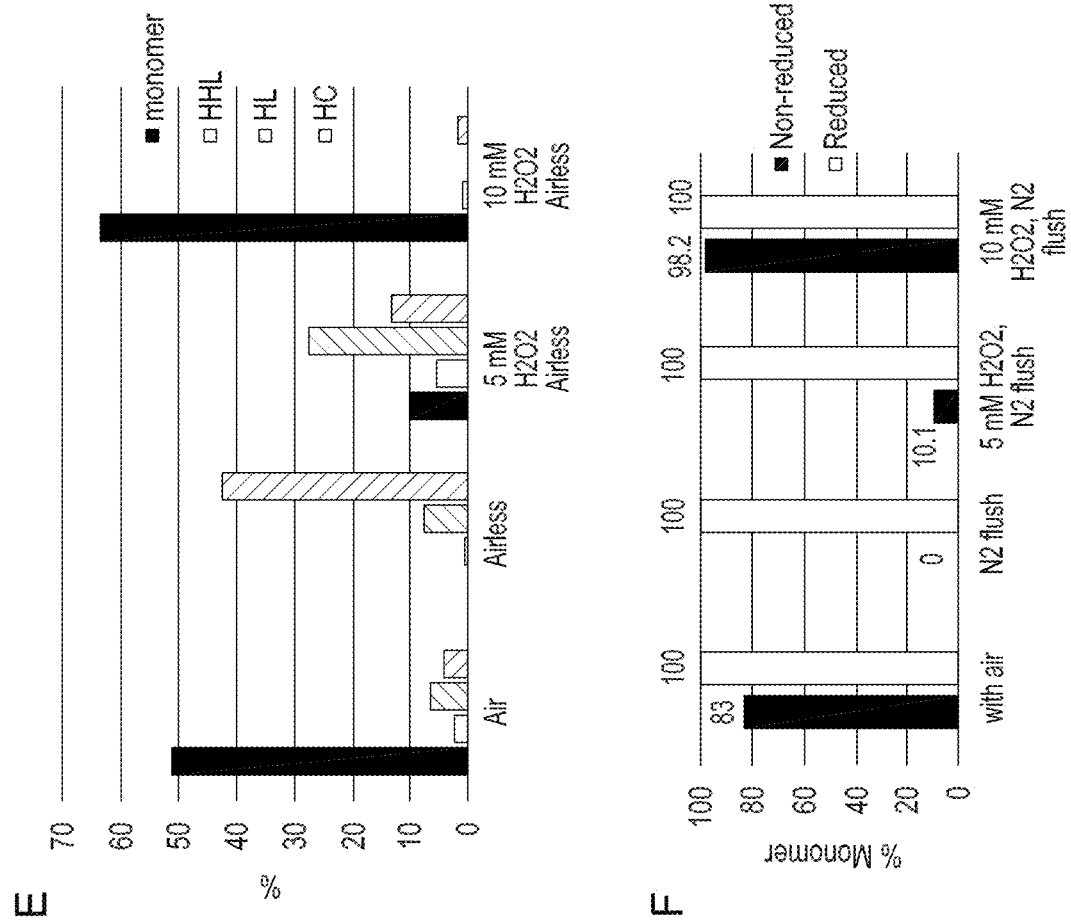

Example 2 shows that there is a low risk of LMW generation if free thiol level is under 100 mM; a free thiol level of 100-200 mM is a warning sign; and free thiol level above 200 mM is a high risk for LMW generation. Many mitigation strategies to prevent antibody reduction have been proposed to either inhibit the enzymes involved in the redox reaction or to oxidize and deplete critical enzyme cofactors, such as NADPH (Mun M 2015, Trexler-Schmidt M 2010). Air sparging has been shown as a robust way to prevent antibody reduction. However, the total free thiol level can still range from micromolar level during manufacturing to millimolar level after holding the CB without air (Table 7). FIG. 8 shows that in the worst case clarified bulk condition, exposure to air could not completely suppress antibody reduction.

The inventors discovered that addition of peroxide to the clarified bulk during harvest prevents antibody disulfide bond reduction and generation of LMW species. Benefits of using peroxide include 1) the peroxide can be mixed with water in any ratio, and 2) removal of excess peroxide should not be a burden for downstream purification. However, while complete decomposition of a 10 mM solution of hydrogen peroxide ($H_2O_2$) to water and oxygen can theoretically generate 5 mM oxygen, this process is slow in the absence of catalysts.

Example 2 shows that addition of hydrogen peroxide, or alternative inorganic or organic peroxides such as sodium percarbonate or sodium perborate, to the clarified bulk can effectively prevent antibody disulfide bond reduction.

In one embodiment of the invention, antibody disulfide bond reduction is prevented by adding hydrogen peroxide to the clarified bulk at harvest.

In one embodiment of the invention, antibody disulfide bond reduction is prevented by adding inorganic or organic peroxides such as sodium percarbonate or sodium perborateto the clarified bulk at harvest.

In another embodiment of the invention, antibody disulfide bond reduction is prevented by maintaining the hydrogen peroxide concentration of the clarified bulk at harvest at ≤10 mM.

In another embodiment of the invention, antibody disulfide bond reduction is prevented by maintaining the hydrogen peroxide concentration of the clarified bulk at harvest between 3 mM and 10 mM.

EXAMPLES

Example 1

Vitamin B12 Association with mAbs
Protein Stocks

Two different therapeutic IgG4 molecules (mAb A and B) were used in this study. Both of them have single point mutation of serine to proline in the hinge region motif CPSC of original IgG4 to resemble IgG1 interchain disulfide bond structure (Liu H et. al.: MAbs 2012, 4 (1):17-23; Aalberse R C et. al. Immunology 2002, 105 (1):9-19). The IgG4 antibodies were produced in CHO cells and affinity purified using protein A chromatography, additional polishing chromatography and final UF/DF filtration to a histidine-based buffer. Protein concentration of drug substance (DS) was determined by absorption at 280 nm.

Vitamin $B_{12}$ ELISA.

The determination of the amount of vitamin $B_{12}$ (VB12) associated with purified protein was used a commercial VB12 measurement kit (Monobind Inc., Lake Forest, CA) with manufacturer's recommended procedures.

In Vitro Vitamin $B_{12}$ Binding to Drug Substance.

The mAb A or mAb B solution (50 mg/ml) in a histidine based buffer was mixed with either CN-Cbl (Sigma-Aldrich, V2876, stock solution 1 mg/ml water) or HO-Cbl (Sigma-Aldrich, V5323, stock solution 1 mg/ml water) at a molar ratio 4:1 to 2:1 (protein: VB12). The reaction was at room temperature and in dark for 1 day. Buffer exchange with phosphate saline buffer (PBS, Sigma-Aldrich, D5652) was achieved via a 50 kDa cut-off Amicon centrifugal filter until no visible color in flowthrough. The buffer-exchanged reaction solution was subjected to peptide mapping analysis.

Hydrogen Peroxide Oxidation of Reduced Antibody.

One lot of mAb A was partially reduced disulfide bonds during manufacturing. The drug substance was mixed with 0.1% hydrogen peroxide (30 mM) for 4 hours at room temperature and excess hydrogen peroxide was removed by buffer exchange as above mentioned.

Light Exposure Studies.

Freshly prepared medium for mAb A was used in light exposure study. CN-Cbl was added to a final concentration of 10 mg/L (from a 1 mg/ml stock solution).

Figure 4:
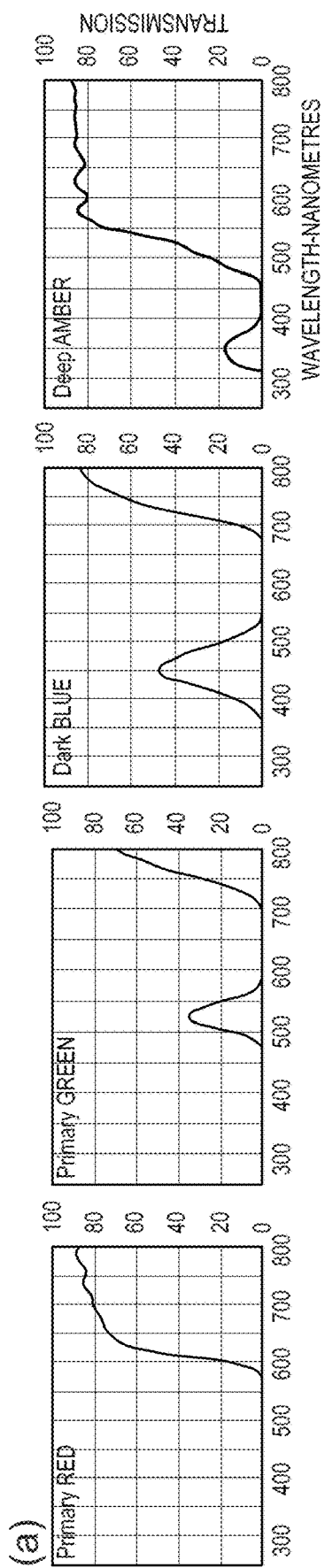
FIG. 4A-4E show the light transmittance spectra of the color filters used in Example 1 (4A). Chromatograms for separation on RP-UPLC and detection at 360 nm of (4B) CN-Cbl and HO-Cbl in standards; (4C) fresh culture media for mAb A; (4D) media exposed to red colored light; and (4E) media exposed to green colored light. In (4D and 4E), the thin, medium and thick lines represented exposure energies of 0.3, 0.6, and 1.2 million lux hr, respectively.
Figure 4:
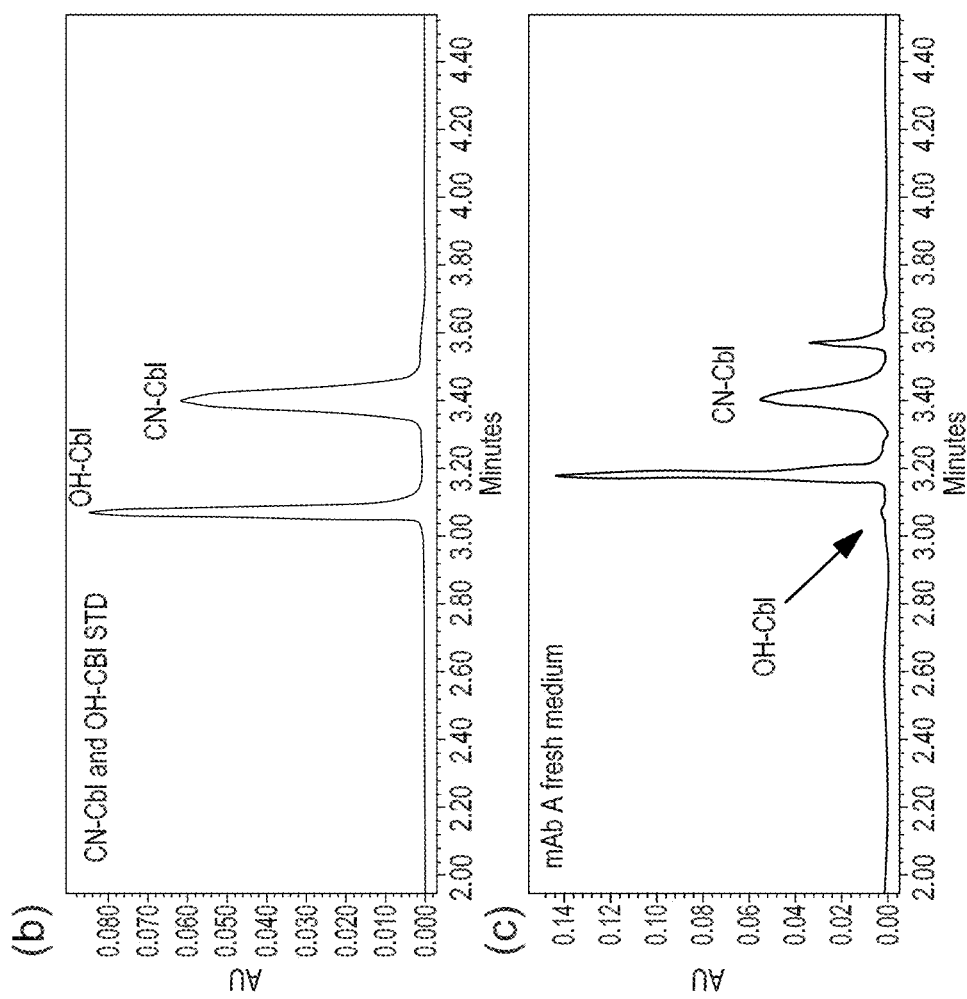
Figure 4:
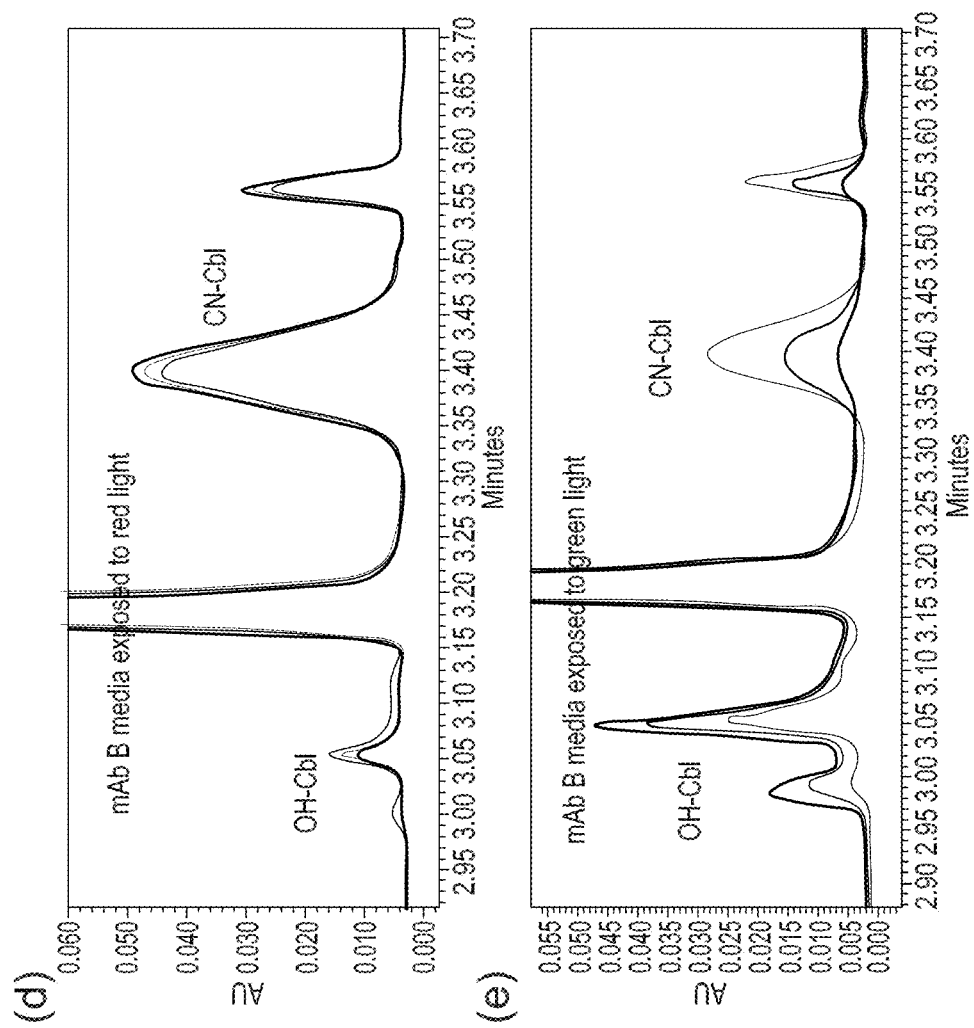

A 13W white light compact fluorescence light bulb (CFL) was used as the visible light source. A 13W commercially available black light bulb centered at 360 nm was used as the UV-light source. The lamp was set up a fume hood with 200 cubic foot air per minute flow rate to avoid heating of the solutions. The bench surface was dark to avoid light reflection. Samples were placed about 12-13 inches away from the lamp (average intensity was 672 lux on the surface of tubes) to simulate normal room light conditions (500-1,000 lux). Light intensities were measured by light meters (Sper Scientific UVA/B light meter Model 850009 and Extech HD400 for UVA and visible light, respectively). Color filters were purchased from Arbor Scientific (Kit 33-0190). The transmittance spectrums of the filters are shown in FIG. 4. A polycarbonate plastic sheet (2.4 mm in thickness) was purchased from a hardware store and used to filter UVA light out.

All the media samples were exposed to the light source and sampled at 0.3, 0.6, and 1.2 million lux hr (intensity× time of exposure) for visible light or 71 and 212 Watts per square meter for UVA light.

Free Sulfhydryl Group Assay.

The method uses Ellman's reagent, 3,3'-dithio-bis(6-nitrobenzoic acid), 3-Carboxy-4-nitophenyl disulfide; 2,2'-Dinitro-5,5'-dithiobenzoic acid (DTNB) with slight modification from literature (Amer E S et. al. Methods Enzymol 1999, 300:226-239). Briefly, 10 μL sample of drug substance mixed with 15 μL of TE buffer (50 mM Tris-HCl, 20 mM EDTA, pH 7.6) in a 96-well plate. DTNB solution (5 mg/ml in ethanol, from Sigma-Aldrich, D8130) was freshly mixed with 8 M guanidine-HCl in 0.2 M Tris (pH 8) at volume ratio 1:9 before use. Then 100 μL of the DTNB/guanidine solution was added into each well and mixed. Spectral absorption at 412 nm was measured and molar extinction coefficient value of 13,600 $M^{-1}$ $cm^{-1}$ was used for calculation.

Antibody Denaturation Tests.

For heat denaturation, 1 mL of mAb A (after protein A affinity column purification and neutralized with Tris) was heated at 80° C. for 20 minutes in an Eppendorf test tube. Visible precipitation was formed after heating and cooling down. The tube was centrifuged at 18,000× g for 20 minutes. Supernatant was used for protein assay (OD 280) and vitamin $B_{12}$ ELISA assay. For SDS denaturation, 0.25 mL of drug substance was mixed 0.75 mL of 0.3% sodium dodecyl sulfate (SDS) in phosphate saline solution (PBS) and left at room temperature for 1 day. Extra SDS was removed by buffer exchange with PBS via a 50 kDa cut-off Amicon centrifugal filter.

Peptide Mapping Analysis of the Drug Substance-Vitamin B12 Reaction Mixture Using LC/MS/MS.

The sample containing mAb A and vitamin $B_{12}$ was digested with trypsin without prior reduction or alkylation. The buffer exchanged reaction mixture was diluted to 1 mg/mL using the digestion buffer (50 mM tris HCl, 10 mM calcium chloride and 2 M urea, pH7.6) before trypsin was added at an enzyme to protein ratio of 1:25 (weight/weight). After incubation at 37° C., the digested mixture was directly subject to LC/MS/MS analysis. Approximately 10 μg of the tryptic digest was chromatographically separated using a Waters Acquity™ UPLC before being analyzed by a ThermoFisher Q-EXACTIVE PLUS Orbitrap mass spectrometer. A Waters Acquity BEH CSH™ C18 column (1.7 μm, 2.1×100 mm) was used for separation (at 45° C.). A linear gradient of 1% to 80% mobile phase B over 60 mins was used to elute the peptides (mobile phase A: 0.1% formic acid and 5 mM ammonium formate) in water; mobile phase B: 0.1% formic and 5 mM ammonium formate in acetonitrile) at a flow rate of 0.2 mL/min. The Orbitrap mass spectrometer was operated in the positive ion mode with a spray voltage of 3.0 kV. The heater temperature and capillary temperature were set at 300° C. and 275° C., respectively. MS acquisition was performed with a resolution of 70,000 and the 10 most intense ions in each duty cycle were selected for MS/MS analysis with a resolution of 17,500. The dynamic exclusion feature was enabled. Normalized collision energy of 25 was used to obtain fragmentation spectra.

Both disulfide reduced mAb and HO-Cbl are necessary to generate pink color. During manufacturing of mAbs, it was observed that pink color usually appeared at Protein A elute step, in which the mAbs was concentrated and background color from media compositions were removed. We analyzed vitamin $B_{12}$ content by ELISA method and found that the pink colored lot has about 20-fold higher vitamin $B_{12}$ than a colorless batch (Table 1, Batches 1 versus 2).

TABLE 1

Vitamin B12 (VB12) attachment and free thiols of mAh B

| Conditions of mAb B | VB12 (pg/ml) | protein (mg/ml) | VB12 (pg/mg) | # free sulfhydryl group per protein molecule* |
|---|---|---|---|---|
| Batch 1, no pink color | 1.10E+05 | 12.3 | 8.90E+03 | 0.2 |
| Batch 2, pink color | 2.70E+06 | 14.8 | 1.80E+05 | 2.2 |
| Batch 2, heat denatured 85° C. × 20 min/supernatant | 9.50E+04 | 0 | NA | ND |
| Batch 2, after treated with 0.3% SDS and buffer exchange | 1.00E+06 | 3.2 | 3.10E+05 | ND |

Based on molecular weights and concentrations of vitamin $B_{12}$ and the mAb, the colored material had approximately one vitamin $B_{12}$ molecule in 47 mAb molecules. Vitamin $B_{12}$ has three major absorption peaks near 360, 420, and 550 nm. Spectral scanning revealed the pink colored batch had higher absorption than the colorless batch beyond 320 nm (FIGS. 1A and 1B, red vs. purple lines).

It has been proposed that the reduction of disulfide bond and generation of free sulfhydryl groups is associated with the appearance of pink color (Derfus G E et. al. MAbs 2014, 6 (3):679-688). The free sulfhydryl content from the pink colored lot of mAb B had higher free sulfhydryl levels than the colorless batch (Table 1). On the other hand, some batches (N=4 for mAb A and N=2 for mAb B) with high level of free sulfhydryl content did not have pink color in drug substance. For example, Batch 2 of mAb A contained higher level of free sulfhydryl groups than that in Batch 1, but both batches were colorless and had similar levels of vitamin $B_{12}$ (Table 2). These results indicate that free sulfhydryl groups are necessary but alone are not sufficient to generate pink colored product.

TABLE 2

Vitamin B12 attachment and free thiols of mAb A

| Conditions of mAb A | Vitamin $B_{12}$ (pg/mL) | protein (mg/ml) | VB12 (pg/mg) | free sulfhydryl groups per protein* |
|---|---|---|---|---|
| Batch 1, no color | 2.00E+06 | 50 | 4.00E+04 | 0.4 |
| Batch 1 + CN-Cbl | 4.61E+06 | 41.1 | 1.12E+05 | ND |
| Batch 1 + HO-Cbl | 1.92E+07 | 44.5 | 4.32E+05 | ND |
| Batch 2, no color | 1.32E+06 | 50 | 2.64E+04 | 3.1 |
| Batch 2 + CN-Cbl | 1.03E+07 | 42.1 | 2.45E+05 | ND |
| Batch 2 + HO-Cbl | 1.39E+08 | 44..1 | 3.15E+06 | ND |
| $H_2O_2$ treated Batch 2 + HO-Cbl | 7.18E+06 | 33.6 | 2.14E+05 | 0.3 |

Vitamin $B_{12}$ is an essential cofactor for mammalian cell culture. CN-Cbl, the most stable form of vitamin $B_{12}$, is the sole source used in cell culture process. It has been reported that light can convert CN-Cbl to HO-Cbl, which is highly reactive to mAb (Prentice K M et. al.: MAbs 2013, 5 (6):974-981). To demonstrate the need of both free thiols from proteins and reactive HO-Cbl to generate pink color in drug substance, a panel of tests were set up by incubating either CN-Cbl or HO-Cbl with mAb A with low (Batch 1) or high (Batch 2) levels of free sulfhydryl content. The vitamin $B_{12}$ isoforms and mAb were mixed and incubated at room temperature for 1 day in dark. After incubation, free vitamin $B_{12}$ was then removed by filtration. The retained vitamin $B_{12}$ amount (Table 2) indicated that (1) the HO-Cbl is much more active than the CN-Cbl for complexing with the same batch mAb, (2) that the drug substance with a higher level of free sulfhydryl groups was more reactive than the drug substance with the lower level free sulfhydryl groups, and (3) the highest vitamin $B_{12}$ incorporation happened in the presence of HO-Cbl and drug substance with high level of free sulfhydryl group, and resulted in a more than 100-fold increase in vitamin $B_{12}$. The difference in color coming from the vitamin $B_{12}$ amount in each sample was obvious to naked eye (FIG. 2a).

Figure 2:
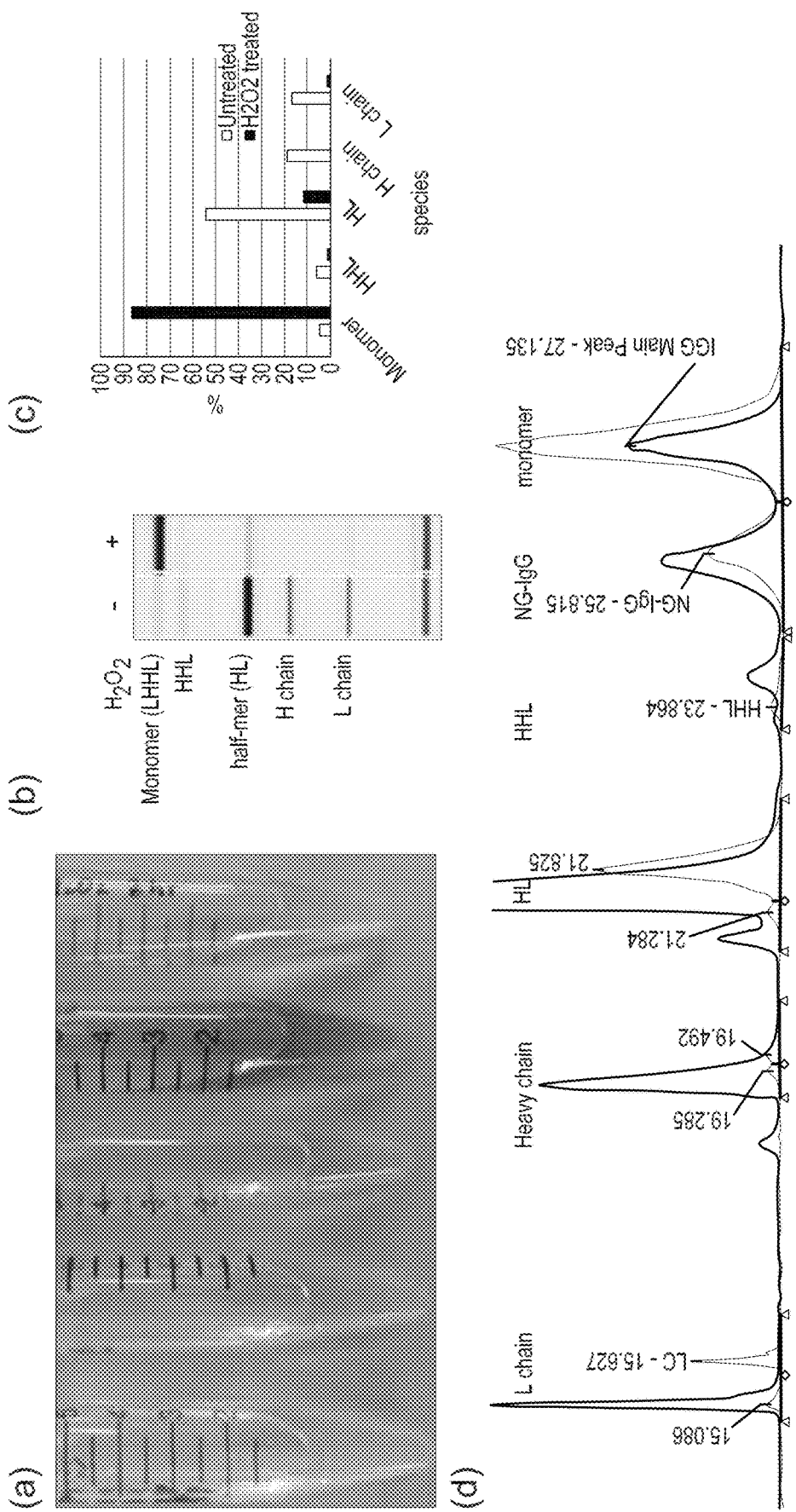
FIG. 2A-2D shows vitamin $B_{12}$ attachment to antibody is a second-order reaction. (2A) Two colorless lots of mAb A, lot with no reduced antibody molecules detected (the "good" lot) and the other has majority of reduced antibody (the "bad" lot) were mixed with either CN-Cbl or HO-Cbl. After incubation, the excess free vitamin $B_{12}$ was removed. Samples from left to right, the good lot and CN-Cbl; the bad lot and CN-Cbl; the good lot and HO-Cbl; the bad lot and HO-Cbl; and the bad lot was treated with hydrogen peroxide first, then mixed with HO-Cbl. (2B) Hydrogen peroxide can oxidize reduced antibody to reform antibody monomer as shown by CE SDS. (2C) Quantification of mAb monomer and various low molecular weight species in hydrogen peroxide treated and untreated mAb shown in 2B. (2D) Non-reduced CE-SDS analysis of mAb A Batch 2 material before (Blue line) and after (Black line) vitamin $B_{12}$ attachment. The individual peak patterns changed before and after incubation with vitamin $B_{12}$ most likely due to oxidation of free sulfhydryl groups and re-formation of disulfide bonds in air.

The free sulfhydryl groups come from reduced disulfide bonds in protein. mAb A batch 2 drug substance had an average 3.1 free sulfhydryl groups per protein molecule (Table 2) and over 95% of the antibody molecules were reduced (FIGS. 2b and 2c). Hydrogen peroxide (0.1% v/v) was added to the Batch 2 material and a majority (86.6%) of the low molecular weight species (LMW) were converted into antibody monomer (FIGS. 2b and 2c). The re-oxidized material had lower free sulfhydryl level (measured after H2O2 treatment and before incubation with HO-Cbl) and lower reactivity toward HO-Cbl. These results demonstrate that the generation of pink color is a second-order reaction whose rate depends on the concentrations of both reactants namely, free sulfhydryl groups and HO-Cbl.

Vitamin $B_{12}$ covalently binds to antibody. Previous literature does not provide experimental evidence of the nature of the vitamin $B_{12}$ attachment, though it was suggested a non-covalent nature (Derfus et al., 2014). The presumed non-covalent association would require antibody structural and charge complementarity to vitamin $B_{12}$ therefore disruption of the native protein structure would release the bound vitamin $B_{12}$. Two denaturation methods, heating and SDS treatments, were used. Heating at 85° C. for 20 minutes caused mAb B pink colored material to become denatured and precipitated. The supernatant, which contained little protein, had only about 3.5% of total vitamin $B_{12}$ of the starting protein solution (Table 1). SDS denatures proteins by binding to the peptide backbone and maintaining denatured protein solubilized in solution. The vitamin $B_{12}$ assay indicated that most, if not all, vitamin $B_{12}$ was still associated with the denatured protein (Table 1). Mobility shift of colored material was detected in a non-reduced capillary electrophoresis-SDS (CE-SDS). Both the initial mAb A drug substance and mAb A-vitamin $B_{12}$ colored complex had multiple bands on non-reduced CESDS due to disulfide reduction. In addition to peaks that overlaid with the correspondent peaks in the initial material, the colored material had additional peaks shifting to higher molecular weight side and the shift was more obvious at low molecular weight peaks, such as single light and heavy chains (FIG. 2d). This observation can be readily explained as addition of vitamin $B_{12}$ molecules to mAb. Collectively, these results deomonstrate that vitamin $B_{12}$ is associated with denatured protein and co-migrates with protein under denatured conditions. Therefore, it is unlikely the interaction between vitamin $B_{12}$ and mAbs is of a non-covalent nature.

Both CN-Cbl and HO-Cbl were observed in the trypsin digest by LC/MS/MS analysis. The theoretical molecular masses for CN-Cbl and HO-Cbl are 1254.567 and 1345.567 Da respectively. The predominant ion observed for CN-Cbl is the double charged ion at m/z 678.293, corresponding to CN-Cbl with an addition of two protons. However, the most predominant ion observed for HO-Cbl is the doubly charged ion at m/z 664.789 corresponding to B12-OH with the OH ligand leaving from the coordination compound and adding a proton. The MS/MS spectra of the m/z 664.789 species from HO-Cbl, and m/z 678.293 from CN-Cbl are shown in FIGS. 4A and 4B, respectively. There are a lot of common fragment ions from the two MS/MS spectra, including m/z values of 147.09, 359.10, 456.72, 912.44, and 1124.45. The m/z 997.48 and 1209.49 in the MS/MS spectra of CN-Cbl is originated from the species with m/z 912.44 and 1124.45, without losing the CoCN group.

Coordinate covalent bonds between cobalamin and the IgG was found through coordination with several Cysteine residues by LC/MS/MS analysis of the tryptic digest. There are five cysteine residues on each light chain and eleven on each heavy chain. However, only five of them (L-C214, H-C134, H-C321, H-367, H-C425) have been observed to form coordination complexes with cobalamin by MS, as listed in Table 3. L-C214 is located at the C-terminal of the light chain and it is the only light chain cysteine residue to be involved in the coordinate covalent bond formation.

TABLE 3

Cysteine containing peptide-cobalamin complex observed in the tryptic digest of the IgG-Vitamin $B_{12}$ reaction mixture

| Cysteine Residue Location | Peptide | Peptide sequence | calculated peptide mass | Calculated mass for Cobalamin-peptide complex | Observed ion for Cobalamin-peptide | Observed mass for Cobalamin-peptide complex |
|---|---|---|---|---|---|---|
| L-C214 | L18-19 | SFNRGEC (SEQ ID NO: 1) | 811.328 | 2139.893 | 13.970 (3+) | 2139.894 |
| L-C214 | L19 | GEC | 307.084 | 1635.648 | 818.327 (2+) | 1635.646 |
| H-C134 | H10 | GPSVFPLAPCSR (SEQ ID NO: 2) | 1229.623 | 2558.187 | 853.402 (3+) | 2558.190 |
| H-C321 | H24 | CK | 249.115 | 1577.679 | 789.345 (2+) | 1577.682 |
| H-C367 | H31 | NQVSLTCLVK (SEQ ID NO: 3) | 1103.601 | 2432.165 | 811.395 (3+) | 2432.169 |
| H-C425 | H36 | WQEGNVFSCSVMHEALHNHYTQK (SEQ ID NO: 4) | 2744.222 | 4072.787 | 1018.953 (4+) | 4072.801 |

This is proved by the masses observed for the C-terminal peptide $L_{19}$-Cbl complex (1635.646 Da) and incomplete digested peptide $L_{18-19}$-Cbl complex (2139.894 Da), within 2 ppm mass accuracy. These coordinate complexes were also confirmed by the MS/MS analysis. The MS/MS spectra of these two peptide-Cbl complex are highly similar, mainly consisting of fragments from the cobalamin. The majority of the MS/MS fragments can be identified by comparing with MS/MS spectra of m/z 664.789 species from HO-Cbl. As shown in FIGS. 4A and 4B, m/z 147.09, 359.10, 486.24 are exactly the same as in the MS/MS spectra of HO-Cbl. Additionally, the species with m/z 971.47 and 1183.48 consist of the same structures with m/z 912.44 and 1124.45, plus a Cobalt (atomic mass 58.93 Da).

Similarly, four Cysteines on the heavy chain have been identified to form coordinate bonds with cobalamin. H-C134 is the counter part of the disulfide bond with L-C214 in the FAB region. The other three Cysteine residues H-C321, HC-C367 and H-C425 are the three C-terminal cysteine on the heavy chain Fc region. Further, HC-C367 and H-C425 are paired disulfide bridge in the native IgG4.

Light conversion of CN-Cbl to HO-Cbl and process control of pink color products. As discussed above, the pink color reaction is a second-order reaction that depends on the concentrations of reduced antibody molecule and HO-Cbl. Therefore, process control strategies are required to prevent reduction of antibody molecule and/or generation of HO-Cbl. The control of reduction of antibody product is a very complicated process which could involve antibody re-design (Peters S J et. al. J Biol Chem 2012, 287 (29):24525-24533; Aalberse R C et. al, 2002), culture media composition (Trexler-Schmidt M et. al. Biotechnol Bioeng 2010, 106 (3):452-461), process parameters (Mun M et. al. Biotechnol Bioeng 2015, 112 (4):734-742) and harvest treatment (Trexler-Schmidt M et. al, 2010). Controlling the amount of the HO-Cbl by avoiding visible light exposure is an alternate strategy. However, these options can cause operation inconvenience and may be cell line specific.

Figure 1:
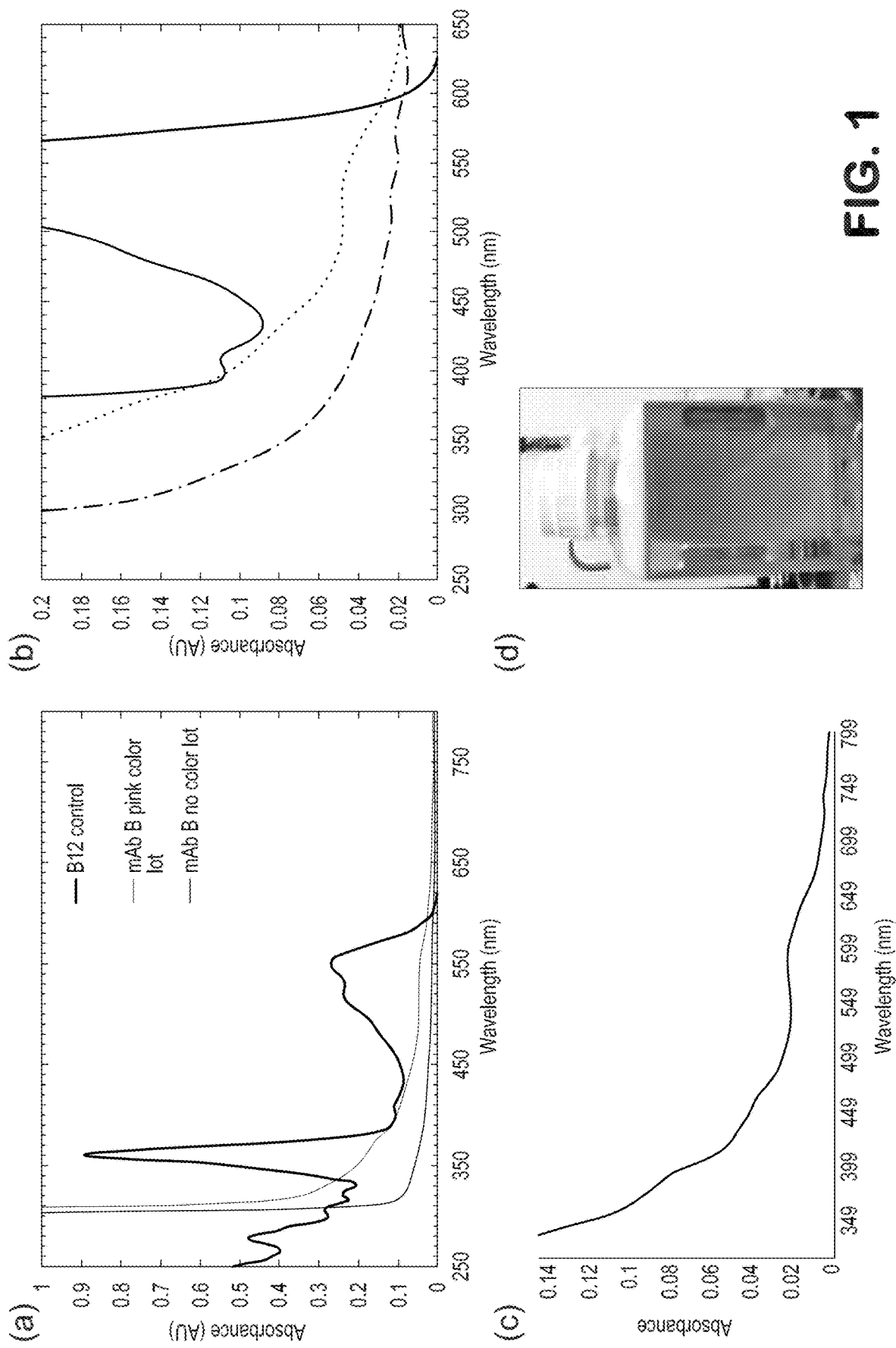
FIG. 1A-1D show the spectral absorption of vitamin $B_{12}$ and two lots of mAb B. 1A is an absorption spectra of vitamin $B_{12}$ and two lots of mAb B. Vitamin $B_{12}$ (cyanocobalamin) at 5 mg/L in PBS (thick line), a pink colored lot (thin line) and a colorless lot (medium line) from 250 to 800 nm. 1B is a re-scaled plot from (1A) to show details. 1D is a bottle of protein A eluate for mAb B that has visible pink color.

We approached this issue by identification of the wavelengths that causes CN-Cbl conversion and set up a control strategy by removing the damaging wavelengths from the light sources. Vitamin $B_{12}$ has both UVA and visible light absorption (FIG. 1). Freshly prepared mAb A culture medium was exposed under either (1) normal laboratory light which is provided from white fluorescence light tubes with intensity of 500-1,000 lux, or (2) intensified visible light provided by a CFL fluorescence light bulb, or (3) intensified UVA light centered at 360 nm. The CN-Cbl and HO-Cbl were separated and quantified by RP-UPLC (FIG. 4B). The results show that it was visible light, not UVA light, that mainly caused CN-Cbl to convert to HO-Cbl (Table 4). The conversion rate was a function of overall illumination (intensity×time) from both normal laboratory light and high intensity visible light.

TABLE 4

Visible light, not UVA light, is responsible for CN-Cbl conversion

| Conditions | Total energy * | VB12 | |
|---|---|---|---|
| | | % CN-B12 | % HO-B12 |
| No light, control | 0 | 100 | 0 |
| Rm light (672 lux), 4 days | 64.5 | 74.0 | 26.0 |
| Rm light (672 lux), 7 days | 113 | 63.8 | 36.2 |
| Rm light (672 lux), 11 days | 177 | 55.0 | 45.0 |
| Rm light (672 lux), 14 days | 226 | 47.8 | 52.2 |
| Vis light (7.3 klux), 1 day | 175 | 64.0 | 36.0 |
| Vis light (7.3 klux), 4 day | 701 | 32.7 | 67.3 |
| Vis light (7.3 klux), 7 day | 1226 | 23.8 | 76.2 |
| UVA light (2.95 Watts/sq · m), 1 day | 70.8 | 83.4 | 16.6 |
| UVA light (2.95 Watts/sq · m), 3 day | 212.4 | 79.0 | 21.0 |

* The energy unit is Klux hour for visible light and Watts/sq. meter for UVA light.

We next investigated the range of visible wavelengths (or colors) that can cause conversion of CN-Cbl as a function of energy. Selected color filters were used to generate light with specified wavelength cutoffs to isolate certain regions of the light spectrum (FIG. 4A). As shown in Table 5, the extent of CN-Cbl conversion as a function of exposure time to different colored light. As polycarbonate glass can block most of the UVA light while being transparent to visible light, it failed to prevent CN-Cbl conversion. Exposure to red light whose wavelength is greater than 600 nm had the slowest rate of CN-Cbl conversion (FIG. 4d). In contrast, both green light (FIG. 4e) and blue light have much higher rates of CN-Cbl conversion. CN-Cbl has absorption peaks at 420 nm and 500-550 nm regions which overlap with blue and green light spectra used in this study. These results provide solid evidence to support our view that different colored light has a different impact on CN-Cbl conversion and only wavelengths greater than <600 nm can cause CN-Cbl conversion.

TABLE 5

Color light impact on CN-Cbl conversion

| Filters | Conditions | % B12-CN | % B12-OH |
|---|---|---|---|
| Control, wrapped in dark | stored at 4 C. until all samples ready for analysis | 95 | 5 |
| wrapped in dark | Room temp, 14 days | 93 | 7 |
| wrapped in dark | Room temp, 26 days | 84 | 16 |
| CFL white light | 0.3 million lux hour | 57 | 43 |
| CFL white light | 0.6 million lux hour | 25 | 75 |
| CFL white light | 1.2 million lux hour | 6 | 94 |
| CFL light, polycarbonate sheet | 0.4 million lux hour | 41 | 59 |
| CFL light, polycarbonate sheet | 0.6 million lux hour | 17 | 83 |
| CFL light, polycarbonate sheet | 1.7 million lux hour | 0 | 100 |
| Primary Red filter | 0.3 million lux hour | 88 | 12 |
| Primary Red filter | 0.6 million lux hour | 83 | 17 |
| Primary Red filter | 1.2 million lux hour | 76 | 24 |
| Primary Green filter | 0.3 million lux hour | 52 | 48 |
| Primary Green filter | 0.6 million lux hour | 23 | 77 |
| Primary Green filter | 1.2 million lux hour | 7 | 93 |
| Dark blue filter | 0.3 million lux hour | 3 | 97 |
| Deep Amber filter | 0.3 million lux hour | 57 | 43 |
| Deep Amber filter | 0.6 million lux hour | 52 | 48 |
| Deep Amber filter | 1.2 million lux hour | 23 | 77 |

Use red color light in manufacturing environment as a control strategy of pink color. The use red light instead of normal white fluorescence light was tested in a laboratory setting. Reduced mAb A (Batch 2 product in Table 2) was spiked into culture media at a similar mAb A concentration as real cell culture at the time of harvest. The culture media had been previously exposed to white light, red or green light (1.2 million lux hour). After overnight (20 hours) incubation in the dark, the mAb was purified by Protein A column and bound vitamin $B_{12}$ was measured by ELISA assay. As shown in Table 6, there was more vitamin $B_{12}$ attachment in both white and green light exposed media than that in the red light exposed and the dark control. These results indicate that red light can indeed protect CN-Cbl from conversion.

TABLE 6 mAb A drug substance spiked into CB exposed to various color light

| Conditions | Protein (mg/ml) | VB12 (pg/mL) | VB12 (pg/mg) |
|---|---|---|---|
| control CB (dark control, 26 day) + DS | 1.57 | 1.38E+04 | 8813 |
| White CFL light CB (1.2 mluxhr) + DS | 1.58 | 1.17E+05 | 73861 |
| Red filter CB (1.2 mluxhr) + DS | 1.56 | 1.36E+04 | 8704 |
| Green filter CB (1.2 mluxhr) + DS | 1.74 | 5.51E+04 | 31646 |

Example 2

Using Hydrogen Peroxide to Prevent Antibody Disulfide Bond Reduction During Manufacturing Process Protein Stocks Two IgG4 molecules (1 and 2) and two IgG1 molecules (3 and 4) were used in this study. The IgG4 molecules had a single point mutation of serine to proline in the hinge region motif CPSC of original IgG4 to resemble the IgG1 inter-chain disulfide bond structure CPPC (Liu H et. al. MAbs. 2012; 4:17-23, Aalberse R C et. al. Immunology 2002; 105:9-19). All the mAbs were produced in CHO cell culture with cell viabilities ranging from 50 to 90%. The clarified bulk (CB) was usually generated with depth filtration unless otherwise specified, in which case it was generated by centrifugation. The mAb 1 cell culture in some cases was treated with low pH plus dextran sulfate before depth filtration. Downstream purification was achieved by Protein A chromatography, additional polishing chromatographic steps and a final ultrafiltration/diafiltration step into a histidine-sugar-based buffer. Protein concentrations were determined by absorption at 280 nm (A280) by a Dropsense-96 spectrometer (Trinean NV, 9050 Gent, Belgium).

Free Sulfhydryl Content (Thiol) Assay

The method used 2,2'-dinitro-5,5'-dithiobenzoic acid (DTNB) with slight modification from the literature (Arner E S et. al. Methods Enzymol 1999; 300:226-239). Briefly, 10 mL sample of clarified bulk or drug substance (DS) was mixed with 15 mL of TE buffer (50 mM Tris-HCl, 20 mM EDTA, pH 7.6) in a 96-well plate. DTNB solution (5 mg/ml in ethanol; Sigma-Aldrich, D8130) was freshly mixed with 8 M guanidine-HCl in 0.2 M Tris (pH 8) at volume ratio of 1:9 before use. 100 mL of the DTNB/guanidine solution was added to each well and mixed. Duplicate samples were tested. Spectral absorption at 412 nm was measured and a molar extinction coefficient value of 13,600 $M^{-1}$ $cm^{-1}$ was used for the calculation of free thiol content.

Figure 6:
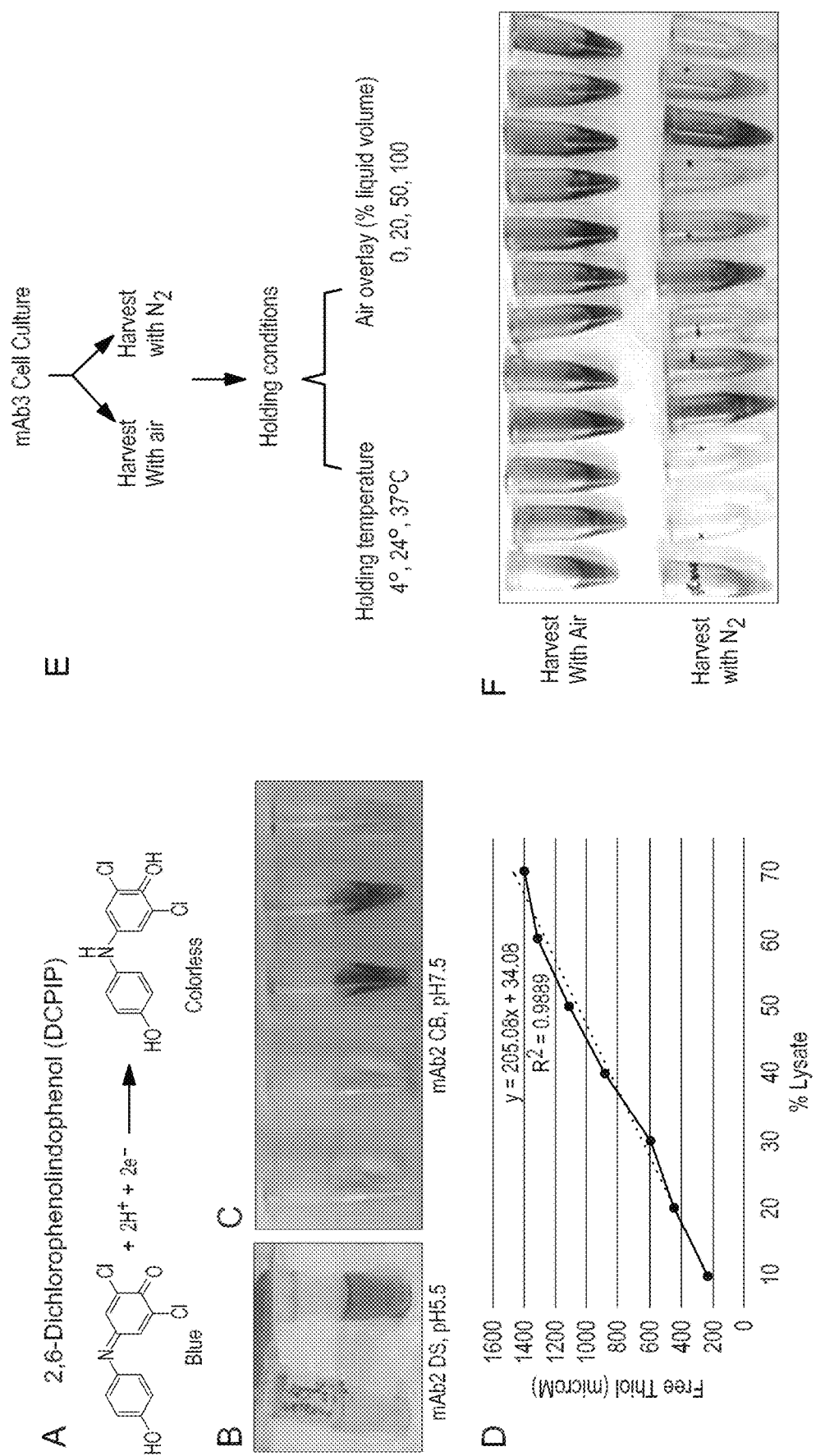
FIG. 6A-6F show the redox indicator DCPIP treatment and observation of color change as a forecasting marker for LMW generation. (6A) Structure and reaction of DCPIP. (6B) mAb2 purified DS samples on the left with >95% LMW (3.1 sulfhydryl groups per antibody protein), showed colorless when treated with DCPIP. mAB2 samples on the right with over 98% intact antibody (0.4 sulfhydryl per antibody protein) showed purple color (in pH 5.5) in the presence of DCPIP. (6C) Color change of DCPIP in CB of mAb 2 from different culture conditions. DCPIP on the left two tubes became completely colorless, indicating higher reducing potential existed the CB; DCPIP in the middle two tubes had blue color, indicating no reducing events; and DCPIP on the right tube became partially reduced. (6D) Free thiol concentrations as a function of mAb 2 percentage of cell lysis. The 100% cell lysate of mAb 2 was mixed with regular CB to generate a dilution curve of cell lysates and free thiol concentrations were measured and reported as the average of duplicate samples. Linear regression equation and R square were calculated with Excel. (6E) Study design to test the order of color change of DCPIP and free thiol amount. (6F) Image of DCPIP test results of the study in Table 7. Samples on top panel received air before and during primary recovery. Samples at bottom had nitrogen gas flushing before and during primary recovery. The order of test tubes from left to right were in the same order as in Table 7 from top to bottom.

Redox Indicator Assays 2, 6-dichlorophenolindophenol (D2932, Spectrum Chemical MFG Corp, Gardena, CA) was dissolved in water to make a fresh 1% stock solution. The oxidized form of 2, 6-dichlorophenolindophenol was blue at neutral pH and became colorless when reduced. In acidic pH, the oxidized form of 2, 6-dichlorophenolindophenol was purple and changed to colorless when reduced. In order to determine the DCPIP color range for reduced and non-reduced samples, 100% mAb 2 cell lysate was mixed with regular clarified bulk produced by centrifugation to generate a series of 0, 3, 5, 10, 20, 30, 40, 50, 60 and 70% dilutions of cell lysate. The free thiol content of each dilution was measured immediately and plotted as a function of the dilution (FIG. 6D). DCPIP (10 mL) was added into the serial cell lysate dilutions (1 mL at room temperature) to determine which dilution showed color change by visual inspection within a duration of a few seconds to minutes.

Non-Reduced and Reduced Caliper

The LabChip GXII Touch HT System (PerkinElmer) was used for mAb purity analysis under both reducing (R_Caliper) and non-reducing (NR_Caliper) conditions according to the manufacturer's recommendation. NR_Caliper was the most convenient, high throughput tool to separate and quantify the antibody fragments, including 2 heavy 1 light chains (HHL), one heavy one light chains (HL), heavy chain (HC) and light chain (LC). Size-exclusion chromatography was used to monitor intact mAb and high molecular weight (HMW) species.

Mass Spectrometric Measurement of Antibody Oxidation for mAb

Samples from mAbs 2 and 3 were reduced by dithiothreitol, alkylated by iodoacetamide and digested with trypsin. The tryptic digest was chromatographically separated using a Waters ACQUITY UPLC system (Milford, MA U.S.A.) before being analyzed by Thermo Scientific Orbitrap Q-EXACTIVE™ PLUS mass spectrometer (Bremen, Germany). A Waters Acquity BEH C18 column (1.7 mm, 2.1 £ 150 mm) was used for separation (at 40° C.). A linear gradient of 2% to 80% mobile phase B over 110 mins was used to elute the peptides (mobile phase A: 0.1% formic acid in water; mobile phase B: 0.1% formic acid in acetonitrile) at a flow rate of 0.2 mL/min.

The Q Exactive Plus mass spectrometer was operating in data-dependent mode to switch between MS and MS/MS acquisition. Ions were generated using a sheath gas flow rate of 40, an auxiliary gas flow rate of 10, a spray voltage of 3 kV, a capillary temperature of 275° C., and an S-Lens RF level of 60. Resolution was set at 70,000 (AGC target 3e6) and 17,500 (AGC target 1e5) for survey scans and MS/MS events, respectively. The dynamic exclusion duration of 10 s was used with a single repeat count. Relative quantitation was achieved by dividing the peak areas of oxidized peptides by the sum of native peptides and oxidized peptides in selected ion chromatograms of the survey scans.

Hydrogen Peroxide and Other Peroxide Treatment

A 30% stock of hydrogen peroxide (Sigma-Aldrich cat. 216763, density of 1.11 g/mL) was freshly diluted with water to 3% stock (v/v, equal to 980 mM) before use. The 3% stock was added to cell culture or CB to final concentrations of 0.1 to 20 mM as desired. To test the effect of hydrogen peroxide on antibody disulfide reduction, hydrogen peroxide stock was added to the CB at final concentrations of 0, 0.1 0.33, 1, 3, 5 10 or 20 mM.

Two inorganic chemicals containing hydrogen peroxide, sodium percarbonate (Sigma-Aldrich, Cat. 371432, 2Na2CO3 3H2O2) and sodium perborate (Sigma-Aldrich, Cat. 372862, NaBO3H2O) were also tested. Both sodium percarbonate and sodium perborate undergo hydrolysis upon contact with water, producing hydrogen peroxide, and carbonate or borate, respectively.

Small-Scale Model of Disulfide Bond Reduction

A 500 mL bottle with an aspirated cap (FlexBioSys, Cat FXB-500M-0005) was filled with 300 mL clarified bulk. Alternatively, a 50 mL BioProcess bag (ThermoFisher, Cat SH30658.11) was filled with 30 mL with clarified bulk. The container was connected to a pure nitrogen gas supply line and flushed with nitrogen gas (≤5 psi) at room temperature for 1 to 2 hours, and then kept enclosed in an airless condition for 1 day. After the hold, the sample was analyzed by the free thiol assay immediately or mixed with iodoacetamide (final concentration 20 mM) before being analyzed by NR_Caliper.

To generate the worst case for antibody disulfide bond reduction, 100% cell disruption was artificially induced by mechanical disruption. The cell culture was centrifuged (500 g for 20 min), the cell pellet was resuspended in 1/10 of original volume in RIPA buffer (ThermoFisher, Cat 8990. 25 mM Tris, 150 mM NaCl, 0.1% SDS, 1% sodium deoxycholate, 1% NP-40, pH 7.6) and lysed at room temperature for 30 minutes with shaking, then chilled on ice and passed through a tissue homogenizer at high speed for 3 min. It was assumed that these steps achieved total cell lysis. The lysed material was then added back to the centrifuged supernatant. This cell lysate was filled into 50 mL bags with or without hydrogen peroxide, then flushed with nitrogen gas and held in an airless condition at room temperature for 1 day as described above. After incubation, the cell lysate was centrifuged twice at 3,000 g for 60 minute at 4° C. and passed a 0.2 micron filter and analyzed as described above.

Hydrogen Peroxide Treatment and its Effect on Product Quality Attributes

For mAb 4, the cell culture fluid from lab-scale bioreactors was used for the following two experiments. In the first experiment, clarified bulk was generated by centrifugation and filtration using a 0.2 micron filter. The resulting clarified bulk was either (a) stored at 4° C. for 4 days as a control or (b) combined with hydrogen peroxide to a final concentration of 10 mM peroxide and stored at 4° C. for 4 days. In the second experiment, hydrogen peroxide was added to the cell culture fluid (with cells), incubated at room temperature for 1 hour before centrifugation. The resulting clarified bulk was either (a) stored at 4° C. for 4 days as a control or (b) placed at room temperature on the third day and flushed with nitrogen gas, and held at room temperature for another day.

All the resulting samples were processed through Protein A chromatography followed by low pH viral inactivation and neutralization steps using process center point conditions. Product quality attributes were evaluated by size-exclusion ultra-performance liquid chromatography to analyze intact antibody and aggregate levels, by imaged capillary isoelectric focusing for charge variants distribution, and by Caliper under both reduced and non-reduced conditions for purity. Process impurities were estimated by ELISA for host cell proteins and by qPCR for residual DNA.

For mAb 2, hydrogen peroxide was added to clarified bulk to a final concentration of 0, 3, 5 and 10 mM, then held at room temperature for 1 day under nitrogen gas flushing. The resulting samples were processed through high throughput Protein A chromatography before analysis.

Disulfide Bond Reduction During Manufacturing

The reduction of mAbs has been observed in process development for several IgG1 and IgG4 antibody molecules in either the clarified bulk (CB) or at Protein A elute (PAE).

As with other groups, we observed accumulation of total free thiol in the clarified bulk during harvest and primary recovery (WO 2015/085003, Ruaudel J, et. al. BMC Proceedings 2015; 9 (9):24). The difference in free thiol concentrations between samples of mAb 1 clarified bulk that showed disulfide reduction versus samples that did not was significant (FIG. 5A). In the case of mAb 1, when the free thiol level in the clarified bulk was below 100 mM, there was low risk of low molecular weight generation; a free thiol level of 100-200 mM posed a potential risk; and free thiol level above 200 mM was a high risk for low molecular weight generation. It is worth noting that Ellman's reagent (2,2'-dinitro-5,5'-dithiobenzoic acid; DTNB) reacts with sulfhydryl groups both from small sulfhydryl-containing molecules, like reduced glutathione, cysteine and lipoic acid, in addition to the free sulfhydryl groups in proteins. Thus the baseline level of free thiol level depends on cell lines, culture media composition (small sulfhydryl-containing molecules) and cell viability. Nevertheless, when the reduction of disulfide bonds occurred, the free thiol level tended to be much higher than baseline.

The level of free thiol in a clarified bulk is very dynamic and pertains to the compositions and handling process. In addition to air exposure, other factors such as storage temperature and pH also contribute to the dynamics. Adjusting the pH of mAb 1 clarified bulk from 7 to 4.8, followed by the removal of cells by depth filtration led to a small decrease in free thiol level and percentage of low molecular weight that was observed (FIGS. 5B and 5C). When the cell harvest was treated with a combination of pH 4.8 and dextran sulfate (0.05 g/L and mixing for 60 minutes followed by centrifugation and filtration), the free thiol level dropped significantly, consistent with the observation that flocculation removes host cell proteins, including Trx/TrxR and Glu/GR and may also remove some small sulfhydryl-containing molecules. The level of free thiol also varied with temperature. Incubation of the control clarified bulk at 37° C. for 75 min caused a 60% drop of free thiol content. However, if 1 mM of NADPH, a necessary component for the TrxR and GR reactions, was added to the solutions before 37° C. incubation, an increase of free thiol level was seen in the control and pH adjusted CB (FIG. 5A). These dynamic changes indicate that the free thiol level should be monitored in the pre- to post-harvest steps in order to better forecast the risk of low molecular weight generation.

Using Redox Indicators to Predict Disulfide Bond Reduction

Since the disulfide bond reduction is a redox reaction, it is possible to use redox indicators as a simple, rapid and robust way to replace the DTNB test and to forecast the potential risk of low molecular weight formation during harvest and recovery. A redox indicator undergoes a definite color change at a specific electrode potential in a similar way as pH indicators undergo a color change at a specific pH. To find the appropriate redox indicator, an array of commercially available redox indicators were tested, and several were identified as the best potential candidates that can be used in biologics manufacturing process.

An example of a redox indicator is 2,6-dichlorophenolindophenol (DCPIP, FIG. 6A). Its color changed in mAb 2 purified drug substance, which had high percentage of low molecular weight (FIG. 6B), and its color can be completely or partially or not changed in clarified bulk with high, medium and low level of free thiols, respectively (FIG. 6C). To determine the DCPIP color change range, the DCPIP stock solution was added to a series dilution of mAb 2 cell lysates with known free thiol concentrations (FIG. 6D). DCPIP underwent a color change in mAb 2 CB with 3-5% cell lysate and free thiol concentrations of 80-100 mM range. Therefore, when a clarified bulk sample had a free thiol concentration higher than 100 mM, the DCPIP changed color and this feature makes DCPIP a rapid and easy-to-use method to forecast the risk of disulfide bond reduction during manufacturing.

A study was designed to examine if the color change in DCPIP correlated with the free thiol levels and was able to correctly predict the generation of low molecular weight (FIG. 6E). The mAb 3 clarified bulk was generated by depth filtration with air or with nitrogen gas flushing of the filter train prior to the processing. The nitrogen gas flushing was used to generate an "airless" condition where there was no oxygen exposed to the fluid during the harvest process. The resulting clarified bulk was aliquoted into small containers with 0, 20, 50 and 100% air overlay headspace volume to liquid volume and incubated at 4° C., 24° C. and 37° C. for one day. As shown in Table 7, the presence of air during harvest and recovery was critical for prevention of low molecular weight generation. In this case, the starting clarified bulk had a lower free thiol concentration (51 mM) compared to the airless condition (207 mM) and the dissolved oxygen (DO) level was sufficient (≥37%) to suppress low molecular weight generation even during holding conditions of percent air overlay and at different temperatures.

TABLE 7

Free thiol concentrations and DCPIP color change in mAb 3 clarified bulk generated and held at various air and airless conditions.

| Air exposure during harvest (Y/N) | Air overlay amount (% of liquid) | Storage temperature | % Air saturation | % CO2 saturation | FreeSHgroup concentration (mM) | DCPIP color change | NR_Caliper % monomer |
|---|---|---|---|---|---|---|---|
| Y | NA | 0 | NA | NA | 51 | NA | 96.5 |
| N | NA | 0 | NA | NA | 207 | NA | 96.5 |
| Y | 0 | 37 | 37 | 6.4 | 36 | Blue | 95.1 |
| Y | 0 | 24 | 91.3 | 7.1 | 42 | Blue | 96 |
| Y | 0 | 4 | 100 | 7.5 | 46 | Blue | 96.3 |
| Y | 20 | 37 | 77.8 | 6.1 | 36 | Blue | 94.9 |
| Y | 20 | 24 | 100 | 6.4 | 46 | Blue | 96.4 |
| Y | 20 | 4 | 100 | 6.9 | 47 | Blue | 96.6 |
| Y | 50 | 37 | 84.1 | 5.3 | 38 | Blue | 95 |
| Y | 50 | 24 | 100 | 6.3 | 47 | Blue | 96.3 |
| Y | 50 | 4 | 100 | 6.9 | 49 | Blue | 96.5 |
| Y | 100 | 37 | 96.1 | 4.7 | 34 | Blue | 94.9 |
| Y | 100 | 24 | 100 | 5.4 | 70 | Blue | 95.8 |
| Y | 100 | 4 | 100 | 6.2 | 49 | Blue | 96.2 |
| N | 0 | 37 | 38.2 | 6.4 | 38 | Blue | 96 |
| N | 0 | 24 | 14.7 | 9.7 | 335 | colorless | 81.6 |
| N | 0 | 4 | 36 | 7.3 | 171 | colorless | 96.3 |
| N | 20 | 37 | 70.1 | 5.5 | 34 | Blue | 95.4 |
| N | 20 | 24 | 62.9 | 7.5 | 84 | Partial change | 96.7 |
| N | 20 | 4 | 92.9 | 6.9 | 121 | colorless | 96.6 |
| N | 50 | 37 | 85.5 | 4.7 | 33 | Blue | 95.7 |
| N | 50 | 24 | 86.3 | 6.6 | 83 | Partial change | 96.1 |
| N | 50 | 4 | 100 | 6.2 | 133 | colorless | 96.8 |
| N | 100 | 37 | 95.4 | 4 | 34 | Blue | 95.6 |
| N | 100 | 24 | 96.6 | 5.4 | 81 | Partial change | 96.5 |
| N | 100 | 4 | 100 | 5.3 | 138 | colorless | 96.2 |

NA: Not applied

Figure 5:
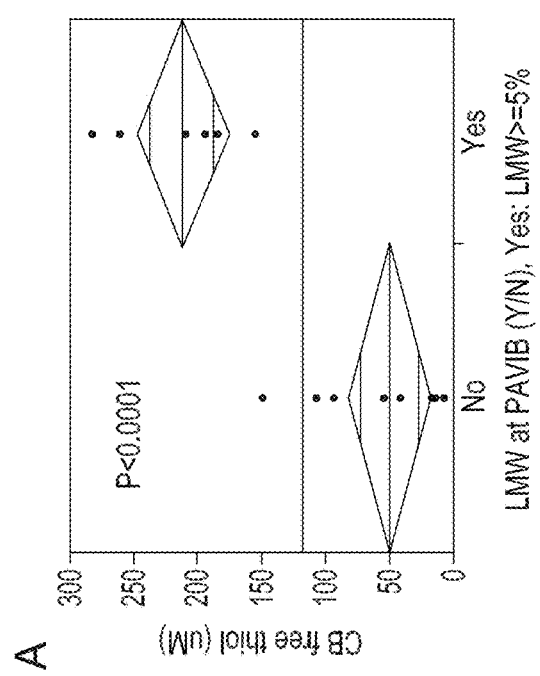
FIG. 5A-5C shows the free sulfhydryl level and low molecular weight (LMW) in CB. (5A) Correlation of free thiol levels of mAb 1 CB samples and LMW presence in the corresponding Protein A purified samples (PAVIB). The PAVIBs were analyzed by NR_Caliper for LMW species. Those samples with LMW ≥5% are labelled as "Yes", otherwise as "No". Analysis was done with JMP software. (5B) Measurement of free thiol levels in CB under different harvest treatments. Clarified harvest bulk (CB) from a lab scale bioreactor (5-L), containing mAb 1 was treated by lowering pH to 4.8 in the absence or presence of dextran sulfate. CB samples were incubated for 1 hour at room temperature before the sample were depth filtered. Post depth filtration, an aliquot of each sample was incubated at 37° C. for 75 minutes with or without addition of 1 mM NAPDH before free sulfhydryl content was measured. A manufacturing lot with high percentage of LMW and a representative lot (normal lot) were also included for comparison. (5C) The percentage of intact antibody for samples in (5B). The intact antibody was measured by NR_Caliper after Protein A purification.
Figure 5:
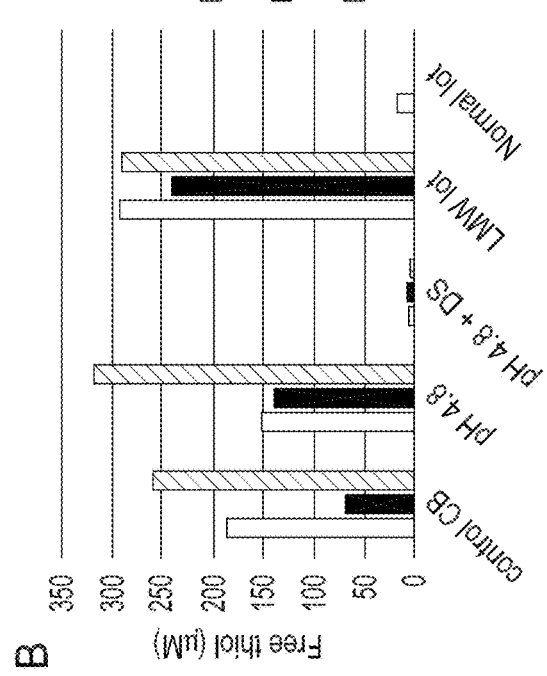
Figure 5:
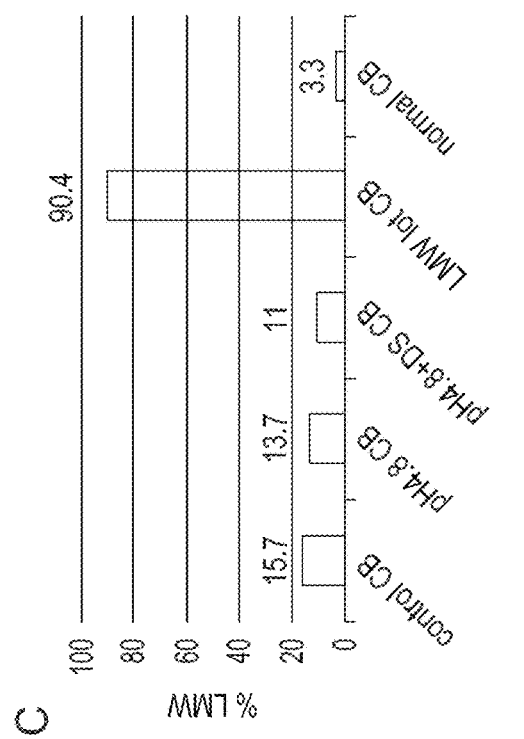

In contrast, the % air overlay during holding became important for the clarified bulk generated in the airless condition. The worst case was an airless harvest and airless holding, where the intact mAb monomer decreased from 96.5% to 81.6%. In addition, when the air overlay was 20% or more, disulfide reduction did not occur. Incubation temperature had a different effect on free thiol concentration. The highest free thiol concentrations and maximal reduction occurred at 24° C. holding. The free thiol amount after 4° C. holding was close to the amount before holding. Holding at 37° C. was presumed to be the optimal temperature for TrxR and GR enzymatic activity. However it universally caused a decrease in the free thiol amounts across all conditions, and the data was consistent with mAb1 results as shown in FIG. 5.

At the end of the 1-day holding study, each sample was mixed with DCPIP stock solution. The color change was assessed by visual observation (FIG. 6F). Table 7 showed that the sequence of color change had strong correlation with free thiol concentrations; the higher the free thiol concentration, the faster the DCPIP color change occurred. All the samples that were harvested in aerated conditions did not show any color change.

Additional redox indicators with different standard reduction potentials were also tested in a similar way, thionine and methylene blue were found to change color at 600-800 and >1,000 mM free thiol levels (data not shown), respectively. These dyes can be put together to comprise a ladder of indicators to rapidly forecast the level of risk during manufacturing.

Figure 7:
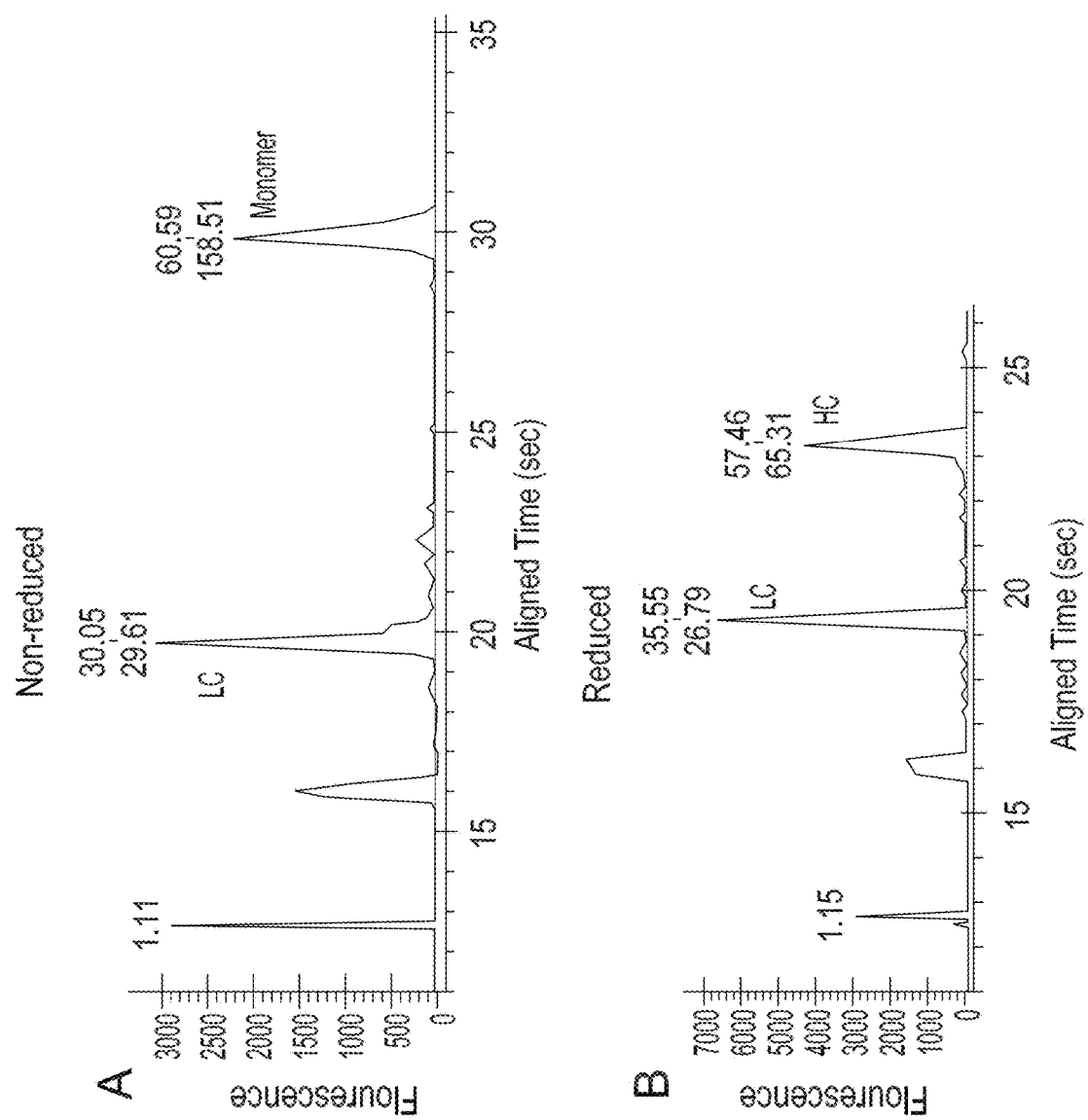
FIG. 7A-7K show using hydrogen peroxide to prevent disulfide bond reduction. The mAb 2 lab scale generated CB was aliquoted into containers with various concentrations of hydrogen peroxide. Airless condition inside containers was generated by nitrogen flushing and was held at room temperature for one day. The resulting samples were analyzed directly by non-reduced (7A, 7C, 7E, 7G, 7I) and reduced (7B, 7D, 7F, 7H, 7J) Caliper without Protein A purification. (7A and 7B) CB with no addition of hydrogen peroxide was exposed to air as control. CB with 0 mM (7C and 7D), 0.33 mM (7E and 7F), 1 mM (7G and 7H), and 3 mM (7I and 7J) hydrogen peroxide was held under airless condition. (7K) Summary of non-reduced Caliper results of mAb fragmentation. Since there was excess light chain of this mAb secreted from host cells. The amount of light chain was not included as a fragment. Abbreviations used for LMW species: LC, light chain; HC, heavy chain; HL, half antibody with one light chain and one heavy chain; HHL, partial antibody with one light chain and two heavy chains.
Figure 7:
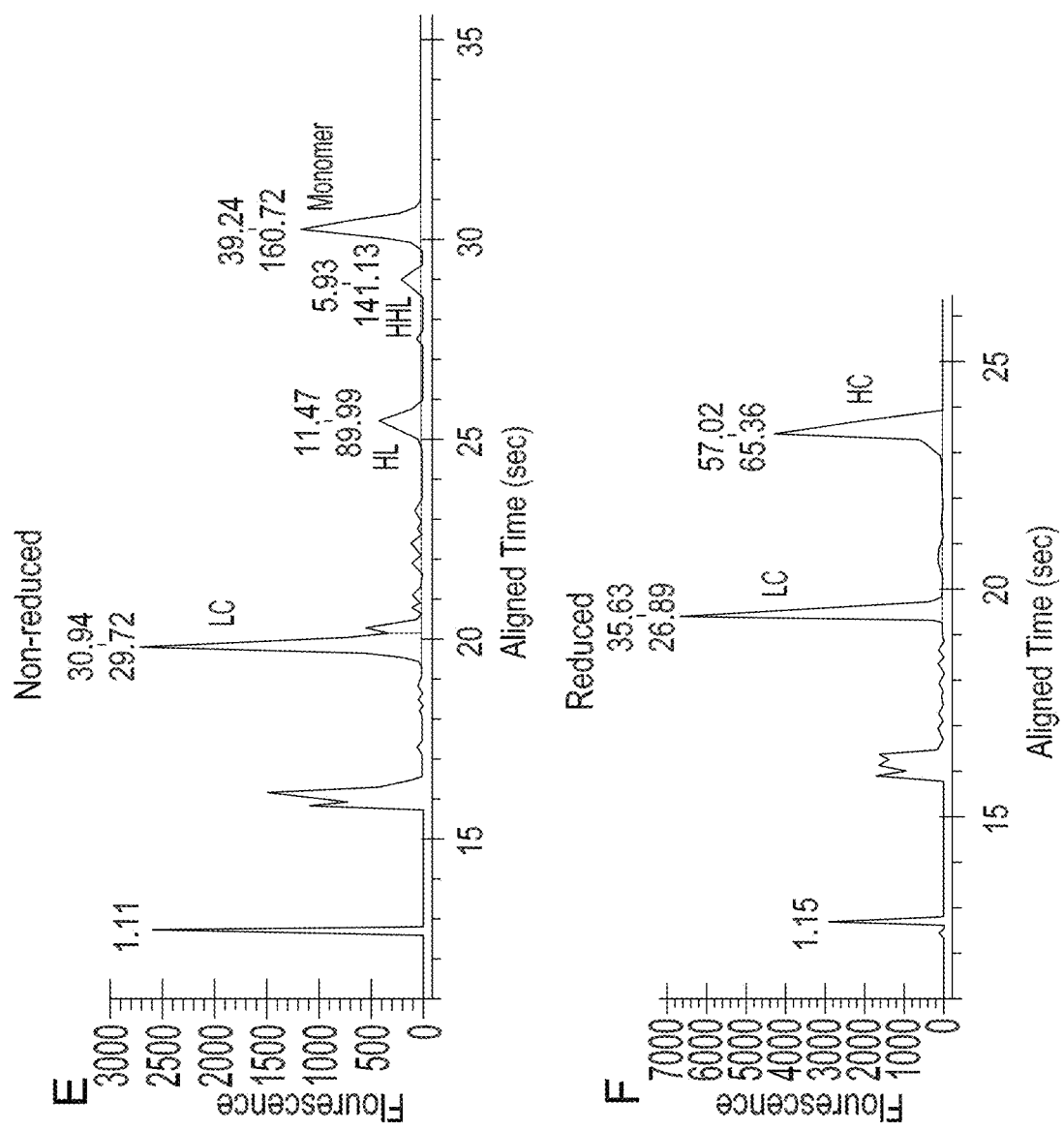
Figure 7:
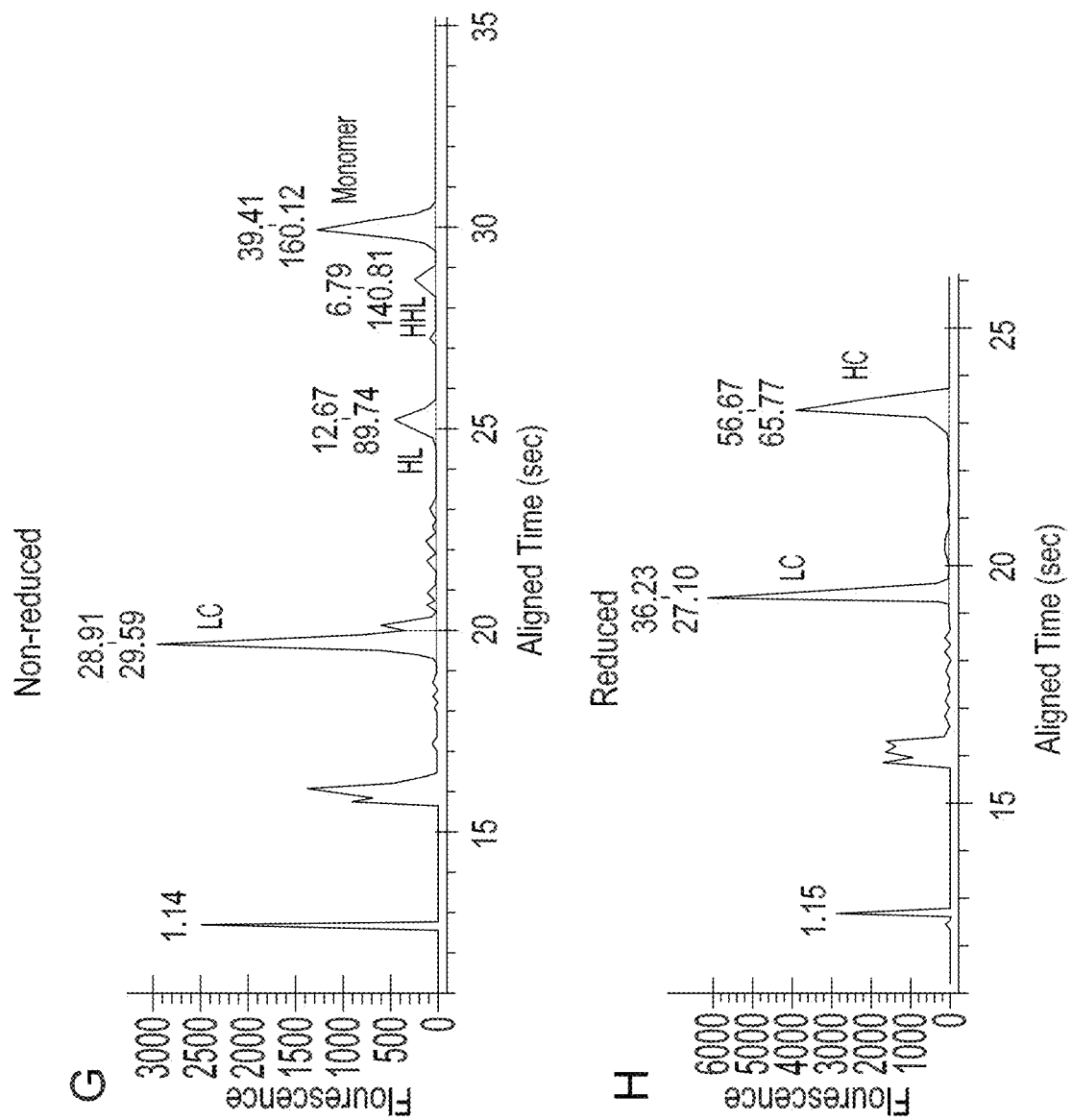
Figure 7:
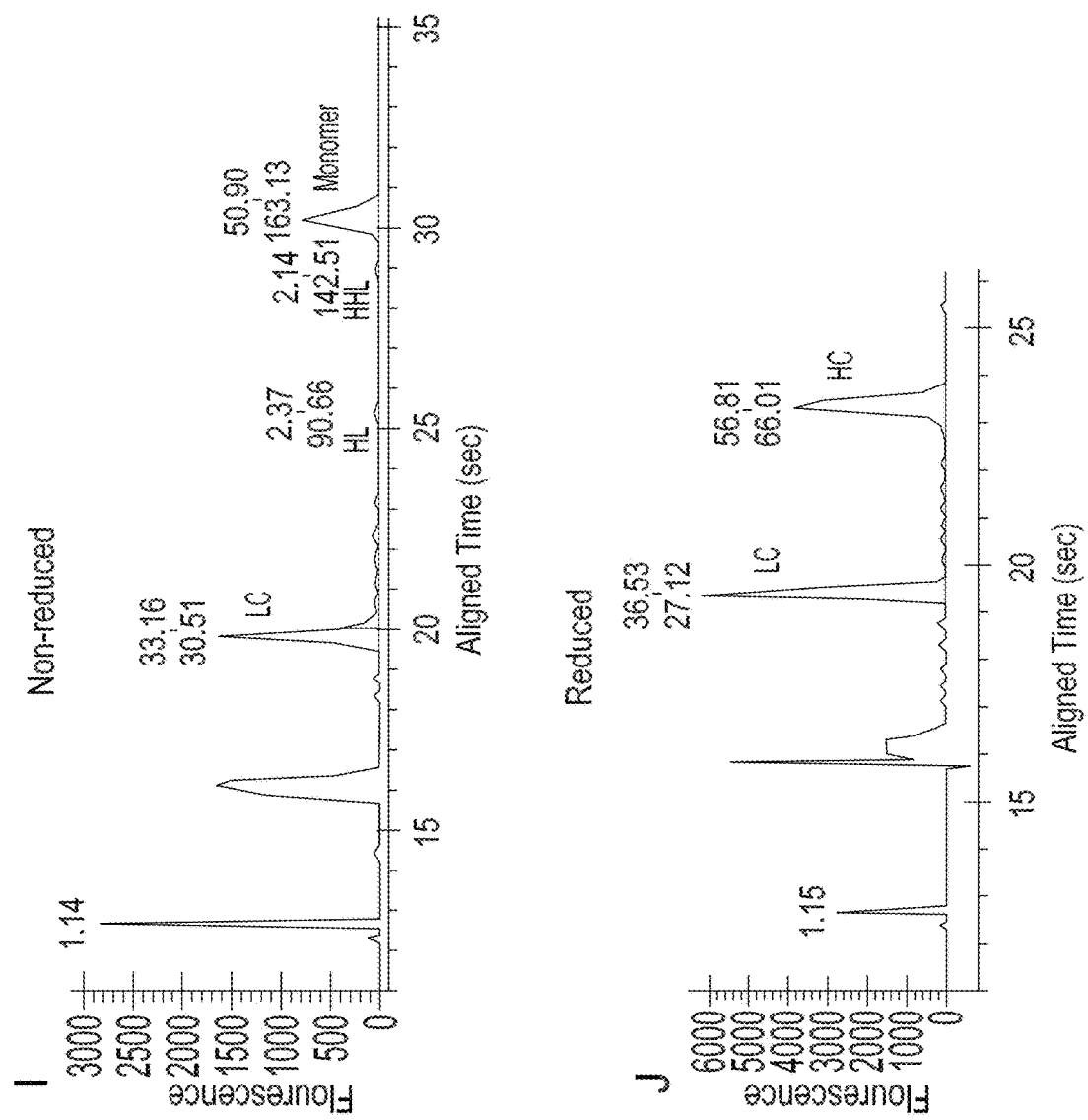
Figure 7:
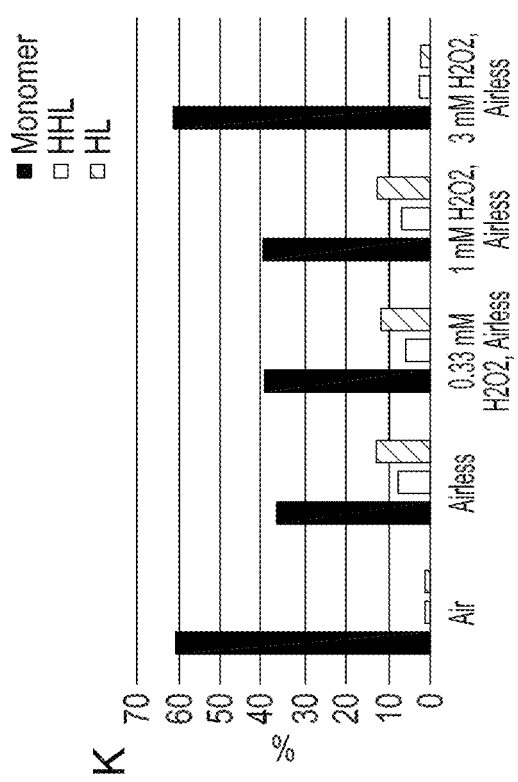

A Scale-Down Model for Recapitulating Disulfide Bond Reduction During Harvest and Primary Recovery A large body of evidence suggests that disulfide bond reduction is correlated with cell lysis during the harvest operation and with the clarified bulk being held in closed containers (e.g. disposable bags) without a sufficient amount of air at room temperature over time (Mun M et. al. Biotechnol Bioeng 2015; 112:734-742). Accordingly, a small scale model was developed to mimic this phenomenon by filling a small amount of clarified bulk (10 to 300 mL) in a sealable container and generating airless conditions by flushing with nitrogen gas and holding at room temperature followed by NR_Caliper analysis for low molecular weight (FIG. 7).

Since clarified bulk from manufacturing operation may vary from lot to lot in term of cell damage and in holding time at various steps from pre-harvest to post-harvest, the low molecular weight content can vary over a wide range from a few percent to near 100%. To simulate small-scale studies, a worst case scenario (described in materials and methods above) was generated in which cellular lysate from CHO cells was mixed with the supernatant from the original volume of cell culture to simulate 100% cell lysis and resulted in generation of low molecular weight even in the presence of air (FIG. 8A), filled into a sealable container, flushed with nitrogen gas and incubated at room temperature for 1 day. Under these conditions, all the intact mAb 2 antibody molecules in clarified bulk became completely fragmented (FIGS. 8B and 9B). The free thiol content in the 100% cell lysis clarified bulk was measured at 1 to 3 mM, which was at least 10 times higher than those from normal operation.

Hydrogen Peroxide can Inhibit the Reduction of Disulfide Bonds

One way to control the reduction of disulfide bonds in mAbs is to eliminate the reducing potential contained in the clarified bulk before mAbs are reduced. The use of H2O2 for this purpose was tested. As shown in FIG. 7, the control mAb 2 clarified bulk generated about 20% low molecular weight after being held in airless conditions at room temperature for 1 day (FIG. 7C). Hydrogen peroxide was added to the same clarified bulk at concentrations of 0.33, 1 and 3 mM prior to airless holding. Results showed that 3 mM (about 0.01%) hydrogen peroxide can completely prevent the generation of low molecular weight (FIGS. 7E, 7G and 7I). These results indicate that hydrogen peroxide effectively prevents disulfide bond reduction.

To determine the minimum concentration of $H_2O_2$ needed to inhibit low molecular weight generation in the worst case, the above described 100% lysed cell culture model was used. In this study, the 100% lysed cell culture was held in airless conditions in the presence of 0, 5 or 10 mM H2O2. After 1 day holding, no intact mAb2 antibody molecules remained and the low molecular weight species were dominated by light and heavy chains with a minor fraction of halfmer, suggesting that the reduction was almost complete as compared to the control sample that was exposed to air (FIGS. 9A and 9B). Adding 5 mM and 10 mM of H2O2 can partially (FIG. 8C) and completely (FIG. 8D) inhibit low molecular weight generation, respectively. These NR_Caliper results from unpurified CB were summarized in FIG. 8E. After Protein A purification, the samples with 0, 5 and 10 mM H2O2 had 0, 10.1 and 98.3% pure antibody monomer, respectively, from NR_caliper results (FIG. 8F). The sample that was exposed in air had 83% pure antibody monomer.

These results confirm that 10 mM H2O2 can effectively prevent mAb reduction in the worst case of clarified bulk processing.

Figure 9:
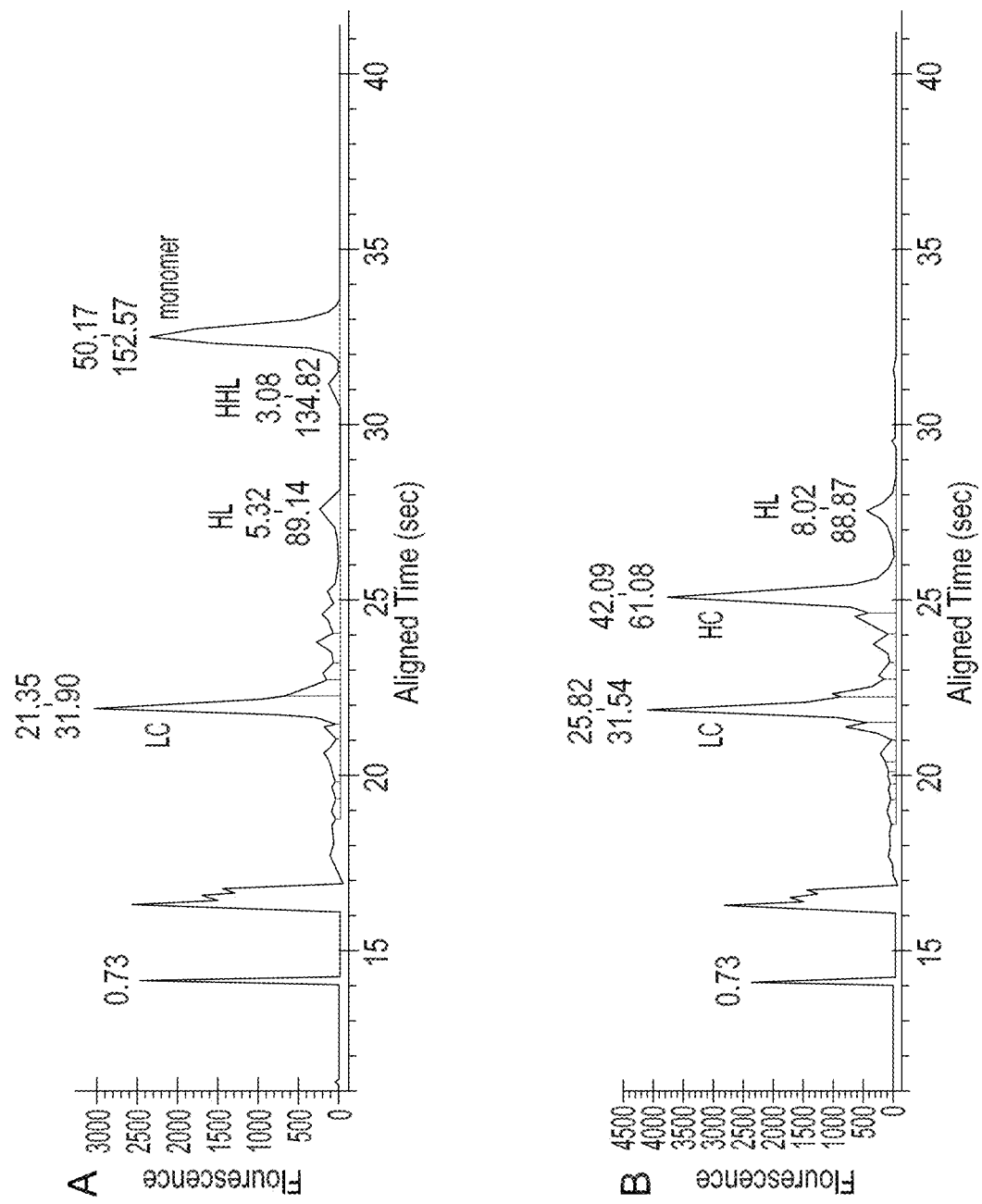
FIG. 9A-9D show the use of alternative peroxides to prevent antibody disulfide bond reduction. Sodium percarbonate and sodium perborate were used in worst case of mAb 2 CB with 100% cell lysis. (9A) CB sample held with air without any peroxides. (9B) CB sample held in airless condition without any peroxides. (9C) A representative result of 5 mM sodium percarbonate-treated CB sample. The sodium percarbonate was added before holding in airless condition. Results came from non-reduced Caliper on unpurified CB (9A to 9C). (9D) Summary sodium percarbonate and sodium perborate treatment. The results came from non-reduced Caliper on unpurified CB.
Figure 9:
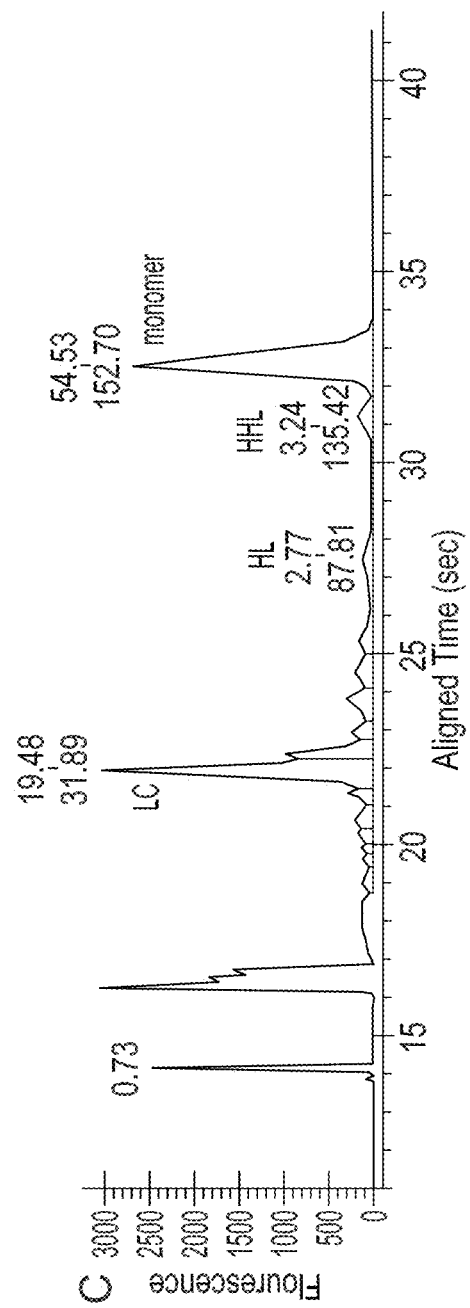
Figure 9:
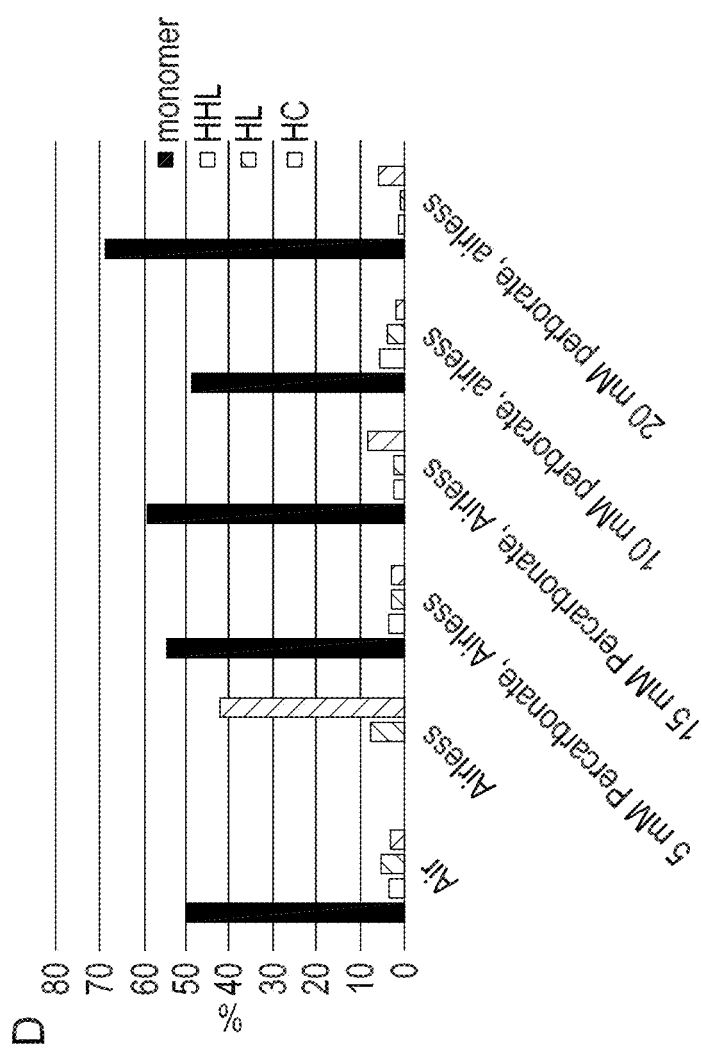

There are many peroxide-containing compounds, inorganic or organic, that can be substituted for hydrogen peroxide. Two inorganic forms, sodium percarbonate and sodium perborate, were tested as a substitute for hydrogen peroxide. The results show that both peroxides can effectively suppress the reduction of disulfide bonds in a concentration-dependent manner (FIG. 9).

Hydrogen Peroxide Treatment and Oxidation of Antibody Molecules

One major concern of using hydrogen peroxide is its potential to oxidize the mAbs. Methionine residues are most susceptible to hydrogen peroxide oxidation. (Luo Q, et. al. J Biol Chem. 2011; 286:25134-25144, Stracke J, et. al. MAbs. 2014; 6:1229-1242) The mAbs 2 and 3 (belonging to IgG4 and IgG1 subclasses, respectively) were analyzed by mass spectrometry for methionine oxidation after various hydrogen peroxide treatments. For both molecules, after addition of H2O2 (1 mM to 10 mM) and incubation at room temperature for 1 day, a small increase in oxidation that was dependent on H2O2 concentration was observed in the same lot of samples that were under the described hydrogen peroxide treatments (Tables 8 and 9). However, the H2O2-induced oxidation changes were insignificant for both mAbs 2 and 3, as the tryptic peptide mapping and LC-MS/MS method has a 1% variation.

TABLE 8

Oxidation of mAb 2 methionine residues after hydrogen peroxide treatment

| mAb 2 Conditions | | | | % Oxidation | | |
|---|---|---|---|---|---|---|
| CB Bioreactor generation | | holding | H2O2 (mM) | % H18ox (M252) | % H30ox (M358) | % H36ox (M428) |
| 1 | centrifuge | No holding | 0 | 5.8 | 2.4 | 2.3 |
| 1 | centrifuge | airless | 0 | 6.1 | 2.7 | 2.3 |
| 1 | centrifuge | airless | 3 | 6.3 | 2.7 | 2.2 |
| 1 | centrifuge | airless | 5 | 6.3 | 2.8 | 2.3 |
| 1 | centrifuge | airless | 10 | 6.4 | 2.8 | 2.5 |
| 1 | depth filtration | air | 0 | 5.4 | 2.5 | 2 |
| 1 | depth filtration | airless | 0 | 5.6 | 2.6 | 2.1 |
| 1 | depth filtration | airless | 5 | 5.8 | 2.7 | 2.2 |
| 1 | depth filtration | airless | 10 | 5.9 | 2.7 | 2.2 |
| 2 | centrifuge | air | 0 | 3.7 | 2.7 | 4.3 |
| 2 | centrifuge | airless | 0 | 3.7 | 2.7 | 4.3 |
| 2 | centrifuge | airless | 5 | 3.7 | 2.8 | 4.7 |
| 2 | centrifuge | airless | 10 | 3.9 | 2.8 | 4.9 |
| 3 | centrifuge | air | 0 | 3.8 | 3.1 | 4.9 |
| 3 | centrifuge | airless | 0 | 3.9 | 3 | 5.3 |

TABLE 9

Oxidation of mAb 3 methionine residues after hydrogen peroxide treatment

| mAb 3 Conditions | | | | % Oxidation | | | | | | |
|---|---|---|---|---|---|---|---|---|---|---|
| CB Bioreactor generation | | holding | H2O2 (mM) | % H3ox | % H10ox | % H12ox* | % H13ox | % H22ox | % H36ox | % H42ox |
| 1 | Depth filtration | no holding | 0 | 0.5 | 1.2 | 0.9 | 1.2 | 1.3 | 1.4 | 0.6 |
| 1 | Depth filtration | airleess | 0 | 0.5 | 1.2 | 0.9 | 1.2 | 1.3 | 1.9 | 0.7 |
| 1 | Depth filtration | airleess | 1 | 0.5 | 1.3 | 1 | 1.1 | 1.4 | 2 | 0.7 |
| 1 | Depth filtration | airleess | 2 | 0.5 | 1.3 | 1 | 1.2 | 1.4 | 2 | 0.7 |
| 1 | Depth filtration | airleess | 3 | 0.5 | 1.3 | 1 | 1.2 | 1.5 | 2 | 0.7 |
| 1 | Depth filtration | airleess | 5 | 0.5 | 1.4 | 1.1 | 1.2 | 1.5 | 2.1 | 0.7 |
| 2 | Centrifuge | air | 0 | 2.9 | 0.7 | ND | 0.9 | 1.5 | 1.7 | 0.5 |
| 2 | Centrifuge | airless | 0 | 2.8 | 0.7 | ND | 1 | 1.9 | 1.7 | 0.5 |
| 2 | Centrifuge | airless | 1 | 2.9 | 0.8 | ND | 0.9 | 1.9 | 1.7 | 0.5 |
| 2 | Centrifuge | airless | 5 | 3.2 | 0.9 | ND | 1.3 | 1.6 | 1.8 | 0.5 |
| 2 | Centrifuge | airless | 10 | 3.6 | 0.9 | ND | 1.2 | 1.7 | 1.9 | 0.6 |

These results indicate that, under optimal peroxide concentrations, mAb oxidation mediated by hydrogen peroxide or other peroxides shows no significant increase, and the level of oxidation can be controlled.

Effects of Hydrogen Peroxide Treatment on Product Quality Attributes

In addition to oxidation, the potential effects of hydrogen peroxide on other drug substance quality attributes and downstream purification process were also evaluated in a lab-scale study. The experimental design included both mAb 2 (an IgG4) and mAb 4 (an IgG1). For mAb 4, the hydrogen peroxide was added to pre-harvest cell culture fluid and post-harvest clarified bulk (without cells). After various hydrogen peroxide treatments, the resulting clarified bulk were processed through Protein A chromatography, followed by low pH viral inactivation and neutralization steps using center process point conditions before analysis. The analytical results for mAb 4, shown in Table 10, indicated there were no noticeable changes in all the attributes that were tested between hydrogen peroxide treated and untreated samples. Process impurities (host cell proteins and residual DNA) were also comparable to the control and acceptable within the process range (data not shown). Similar results were also obtained for mAb 2 that was treated by 0, 3, 5 and 10 mM $H_2O_2$ at room temperature for 1 day (Table 10).

TABLE 10

Hydrogen peroxide treatment on product quality attributes of mAbs 2 and 4.

| Molecule | Conditions* | Purity (%) Reduced | Purity (%) Non-Reduced | Charge variants (%) Main | Charge variants (%) Acidic | Charge variants (%) Basic | Intact mAb (%) Monomer | Intact mAb (%) HMW | LMW | Protein A Step yield (%) |
|---|---|---|---|---|---|---|---|---|---|---|
| mAb4 | Centrifuged CB, 4° C., 4 days | 100 | 96.3 | 50.5 | 46.5 | 2.9 | 95.5 | 4.4 | 0.1 | 94.2 |
|  | 10 mM $H_2O_2$ add to centrifuged CB, 4° C., 4 days | 100 | 96.5 | 49.6 | 47.4 | 3.0 | 95.7 | 4.2 | 0.1 | 94.4 |
|  | 10 mM $H_2O_2$ added to pre-harvest culture fluid, centrifuged, 4° C., 4 days | 100 | 96.7 | 50.3 | 46.4 | 3.2 | 95.5 | 4.4 | 0.1 | 92.6 |
|  | 10 mM $H_2O_2$ added to pre-harvest culture fluid, centrifuged, 4 C., 3 days; $N_2$ flushing, RT for 1 day | 100 | 96.5 | 49.5 | 47.4 | 3.1 | 95.4 | 4.5 | 0.1 | 98.4 |
| mAb2 | Centrifuged CB, $N_2$ flush, RT, 1 day | ND | 99.2 | 49.0 | 18.0 | 33.1 | 98.8 | 1.2 | 0 | ND |
|  | Centrifuged CB, 3 mM $H_2O_2$, $N_2$ flush, RT, 1 day | ND | 99.2 | 50.1 | 16.8 | 33.1 | 98.8 | 1.2 | 0 | ND |
|  | Centrifuged CB, 5 mM $H_2O_2$, $N_2$ flush, RT, 1 day | ND | 99.2 | 46.4 | 19.1 | 34.5 | 98.7 | 1.2 | 0.1 | ND |
|  | Centrifuged CB, 10 mM $H_2O_2$, $N_2$ flush, RT, 1 day | ND | 99.2 | 50.0 | 16.9 | 33.1 | 98.8 | 1.2 | 0 | ND |

*For the mAb 4, the treatments were at either pre-harvest cell culture fluid or clarified bulk steps, the resulting clarified bulk were gone through Protein A chromatography and low pH viral inactivation and neutralization (PAVIB) steps using process center point conditions. The analytical results came from PAVIB samples. For mAb 2, the hydrogen peroxide treated and control clarified bulk samples were purified by high-throughput Protein A columns before analysis.
ND, not determined.

Therefore, these results indicate that hydrogen peroxide treatments (up to 10 mM) have no noticeable changes in all the attributes that were tested in samples treated with hydrogen peroxide before and after cell removal.

We claim:

1. A method for preventing antibody disulfide bond reduction by adding hydrogen peroxide without a coupled reducing agent to clarified bulk during harvest at a concentration greater than zero but not exceeding 10 mM.

2. The method of claim 1, wherein the hydrogen peroxide concentration of the clarified bulk at harvest is maintained at ≤10 mM.

3. The method of claim 2, wherein the hydrogen peroxide concentration of the clarified bulk at harvest is maintained between 3 mM and 10 mM.

\* \* \* \* \*

SEQUENCE LISTING

```
<160> NUMBER OF SEQ ID NOS: 4

<210> SEQ ID NO 1
<211> LENGTH: 7
<212> TYPE: PRT
<213> ORGANISM: Homo sapiens

<400> SEQUENCE: 1

Ser Phe Asn Arg Gly Glu Cys
1               5

<210> SEQ ID NO 2
<211> LENGTH: 12
<212> TYPE: PRT
<213> ORGANISM: Homo sapiens

<400> SEQUENCE: 2

Gly Pro Ser Val Phe Pro Leu Ala Pro Cys Ser Arg
1               5                   10
```

```
<210> SEQ ID NO 3
<211> LENGTH: 10
<212> TYPE: PRT
<213> ORGANISM: Homo sapiens

<400> SEQUENCE: 3

Asn Gln Val Ser Leu Thr Cys Leu Val Lys
1               5                   10

<210> SEQ ID NO 4
<211> LENGTH: 23
<212> TYPE: PRT
<213> ORGANISM: Homo sapiens

<400> SEQUENCE: 4

Trp Gln Glu Gly Asn Val Phe Ser Cys Ser Val Met His Glu Ala Leu
1               5                   10                  15

His Asn His Tyr Thr Gln Lys
            20
```